United States Patent
Noshi

(10) Patent No.: US 12,318,240 B2
(45) Date of Patent: Jun. 3, 2025

(54) NUCLEAR MEDICINE DIAGNOSTIC APPARATUS, NUCLEAR MEDICINE DIAGNOSTIC METHOD, AND STORAGE MEDIUM

(71) Applicant: Canon Medical Systems Corporation, Otawara (JP)

(72) Inventor: Yasuhiro Noshi, Otawara (JP)

(73) Assignee: Canon Medical Systems Corporation, Otawara (JP)

( * ) Notice: Subject to any disclaimer, the term of this patent is extended or adjusted under 35 U.S.C. 154(b) by 148 days.

(21) Appl. No.: 18/192,267

(22) Filed: Mar. 29, 2023

(65) Prior Publication Data
US 2023/0320685 A1    Oct. 12, 2023

(30) Foreign Application Priority Data
Apr. 12, 2022   (JP) ................. 2022-065734

(51) Int. Cl.
*A61B 6/00*    (2024.01)
*A61B 6/03*    (2006.01)
*A61B 6/04*    (2006.01)

(52) U.S. Cl.
CPC ............ *A61B 6/5235* (2013.01); *A61B 6/032* (2013.01); *A61B 6/037* (2013.01); *A61B 6/0407* (2013.01); *A61B 6/5258* (2013.01)

(58) Field of Classification Search
None
See application file for complete search history.

(56) References Cited

U.S. PATENT DOCUMENTS

| 2015/0139515 A1 | 5/2015 | Smith et al. |
| 2022/0036607 A1* | 2/2022 | Balakrishnan .......... G06T 15/08 |

FOREIGN PATENT DOCUMENTS

JP    2015-526708 A    9/2015

* cited by examiner

*Primary Examiner* — Joseph M Santos Rodriguez
*Assistant Examiner* — Tommy T Ly
(74) *Attorney, Agent, or Firm* — Oblon, McClelland, Maier & Neustadt, L.L.P.

(57) ABSTRACT

According to one embodiment, a nuclear medicine diagnostic apparatus includes processing circuitry. The processing circuitry is configured to obtain an X-ray CT image relating to a subject. The processing circuitry is configured to obtain a camera image capturing a position and a shape of the subject corresponding to the X-ray CT image. The processing circuitry is configured to generate an attenuation map based on the camera image and the X-ray CT image. The processing circuitry is configured to obtain detection data based on gamma rays radiating from a radiation source administered into the subject. The processing circuitry is configured to reconstruct an image based on the attenuation map and the detection data.

10 Claims, 23 Drawing Sheets

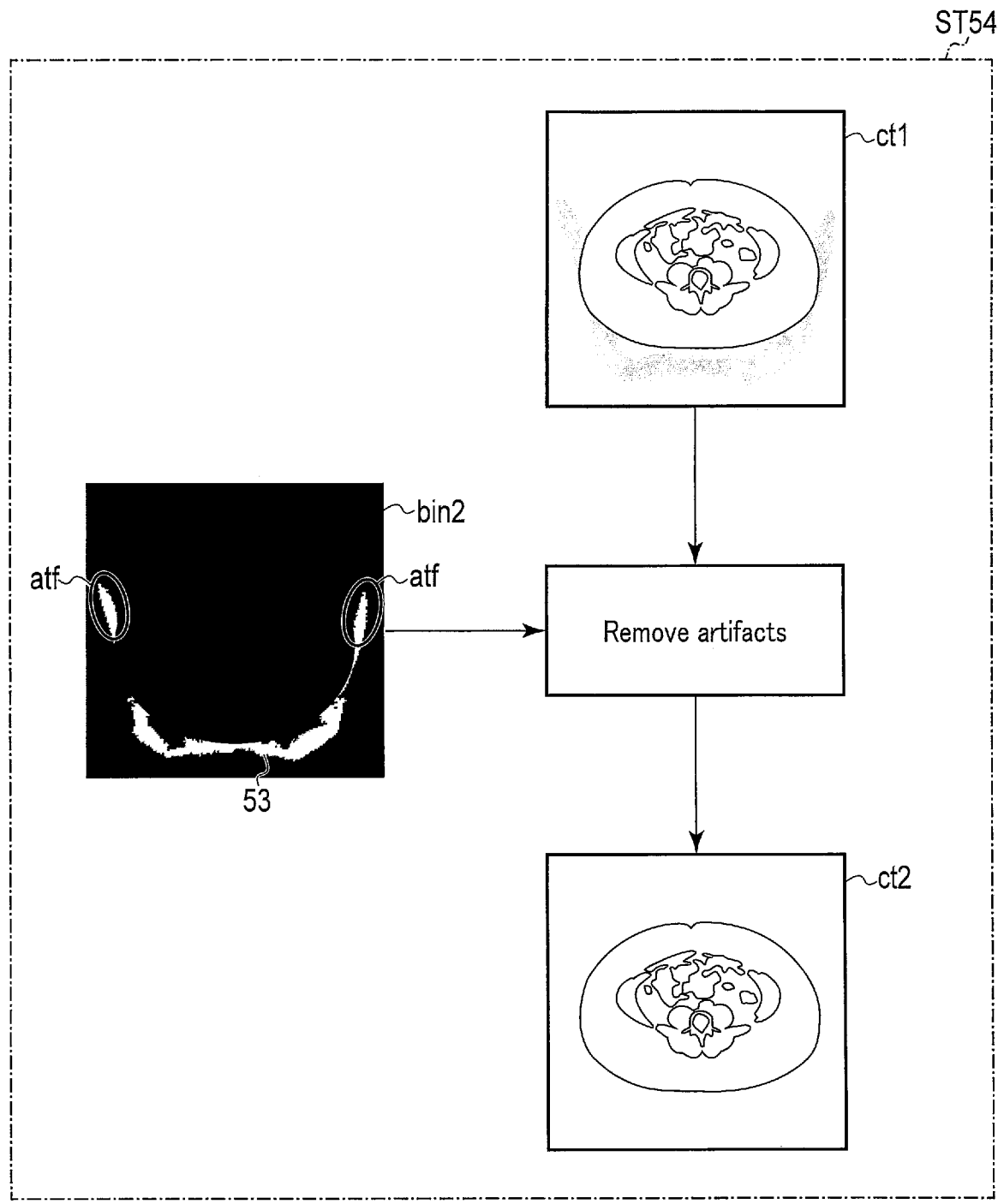
F I G. 9

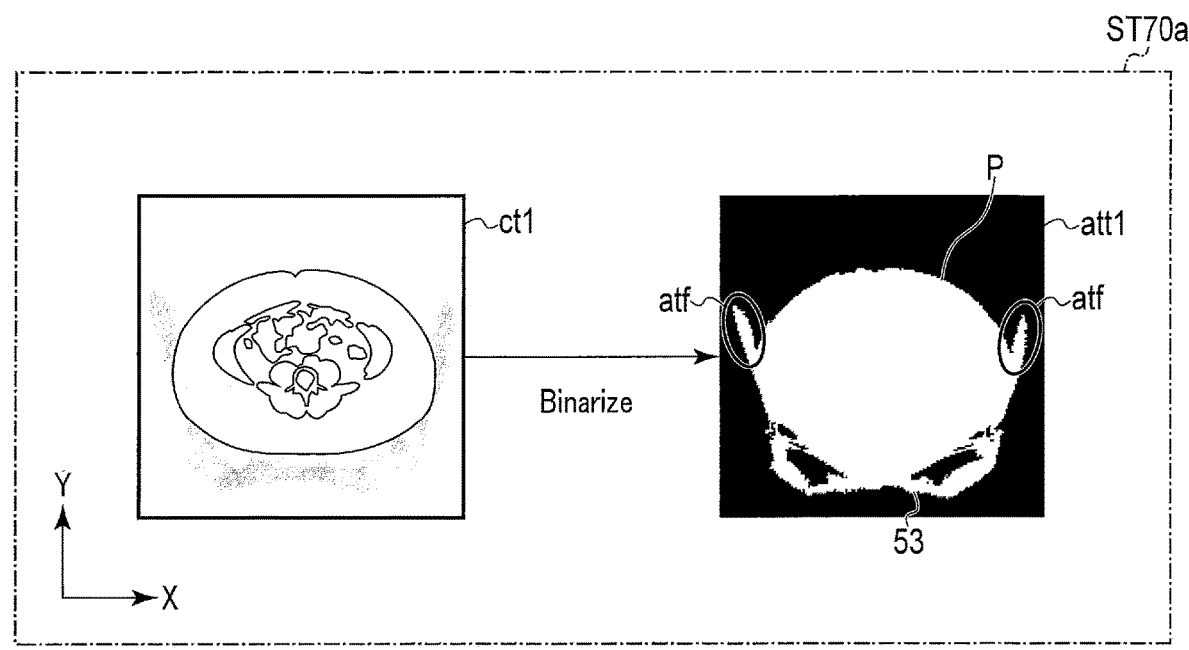
F I G. 12

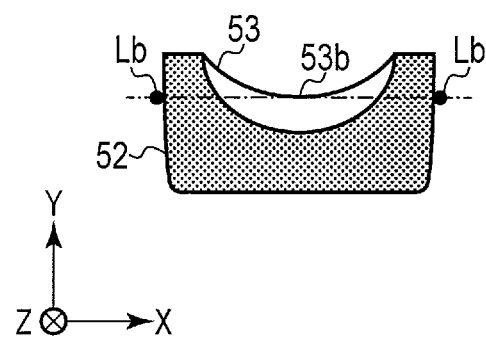
F I G. 19
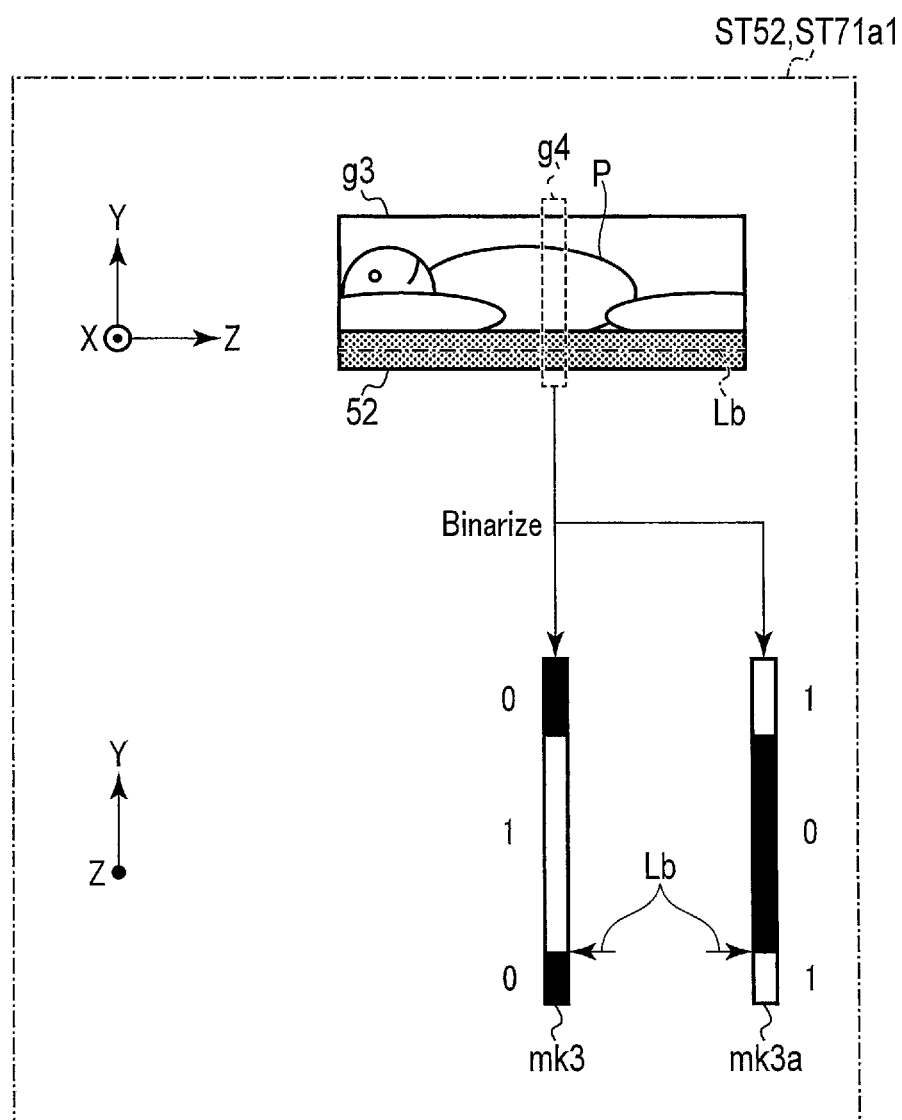
F I G. 20

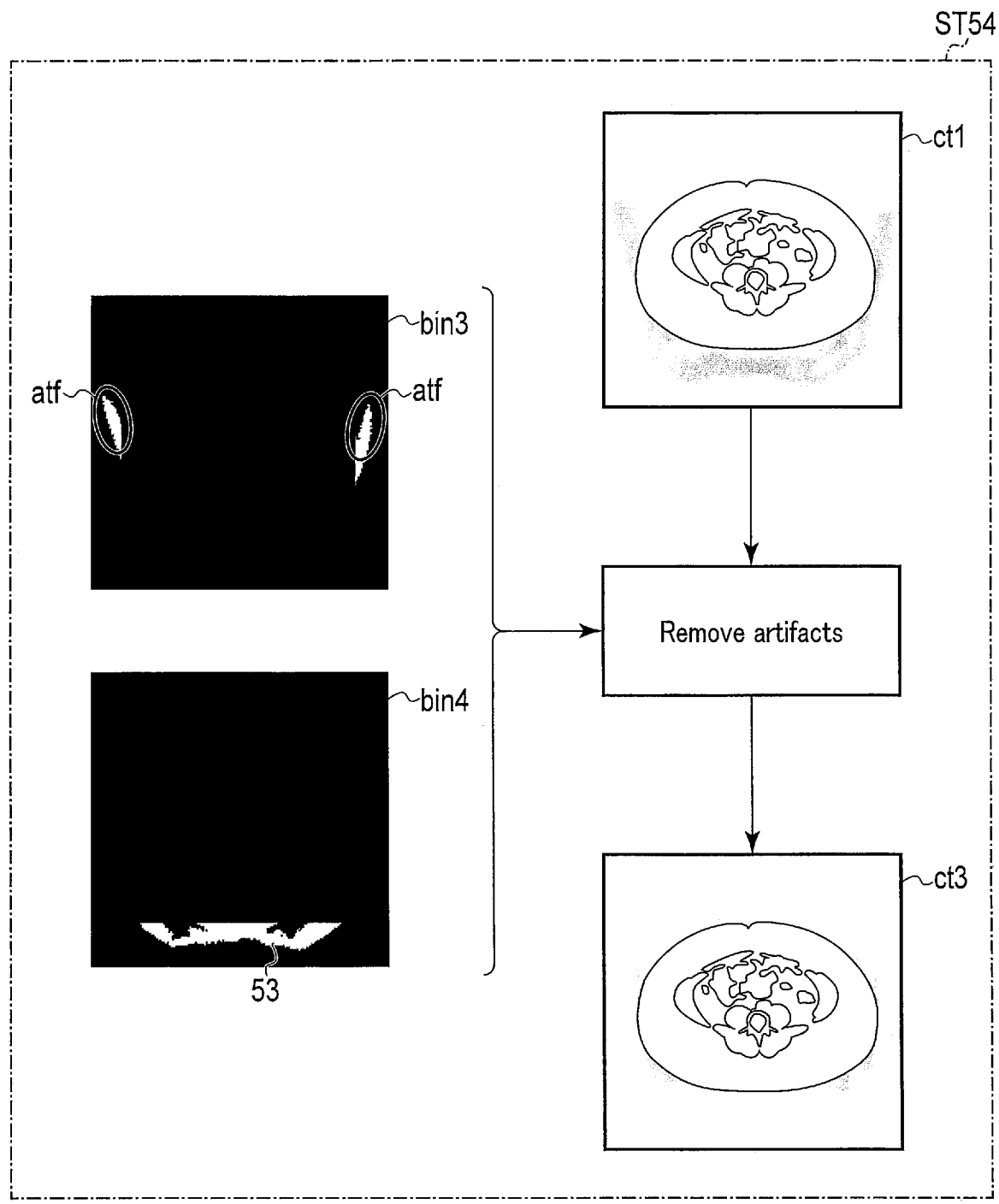
F I G. 22

NUCLEAR MEDICINE DIAGNOSTIC APPARATUS, NUCLEAR MEDICINE DIAGNOSTIC METHOD, AND STORAGE MEDIUM

CROSS-REFERENCE TO RELATED APPLICATION(S)

This application is based upon and claims the benefit of priority from prior Japanese Patent Application No. 2022-065734, filed Apr. 12, 2022, the entire contents of which are incorporated herein by reference.

FIELD

Embodiments described herein relate generally to a nuclear medicine diagnostic apparatus, a nuclear medicine diagnostic method, and a storage medium.

BACKGROUND

In a positron emission tomography (PET)/computed tomography (CT) apparatus, which is a type of nuclear medicine diagnostic apparatus, attenuation correction of a PET image is performed using an X-ray CT image imaged by means of X-ray CT. While a rotating circular detector is used in X-ray CT imaging, a detector arranged on the circumference is used in PET imaging. Thus, in X-ray CT imaging, a large subject may partially protrude from a field of view, causing a missing region at an end of the detector; however, this does not happen in PET imaging. Accordingly, a wider range of image in an XY plane can be reconstructed in PET imaging. In X-ray CT imaging, on the other hand, a sinogram is estimated by inferring a missing region at an end of the detector, and the range of reconstruction is extended to a range equivalent to or larger than that of PET imaging. Such technology is known as "extended reconstruction".

In the extended reconstruction, since a sinogram is estimated, one or more unintended structures such as artifacts may be included in an X-ray CT image reconstructed from the sinogram. In such a case, an adverse effect may be exercised on an image (nuclear medicine image) reconstructed through application of the X-ray CT image. In a PET/CT apparatus, an attenuation map generated from an X-ray CT image, for example, is used for reconstruction of a PET image (nuclear medicine image). This may cause, in the attenuation map, an error resulting from artifacts in the X-ray CT image, and may deteriorate the image quality and the quantitative characteristics of the PET image.

BRIEF DESCRIPTION OF THE DRAWING(S)

Figure 4:
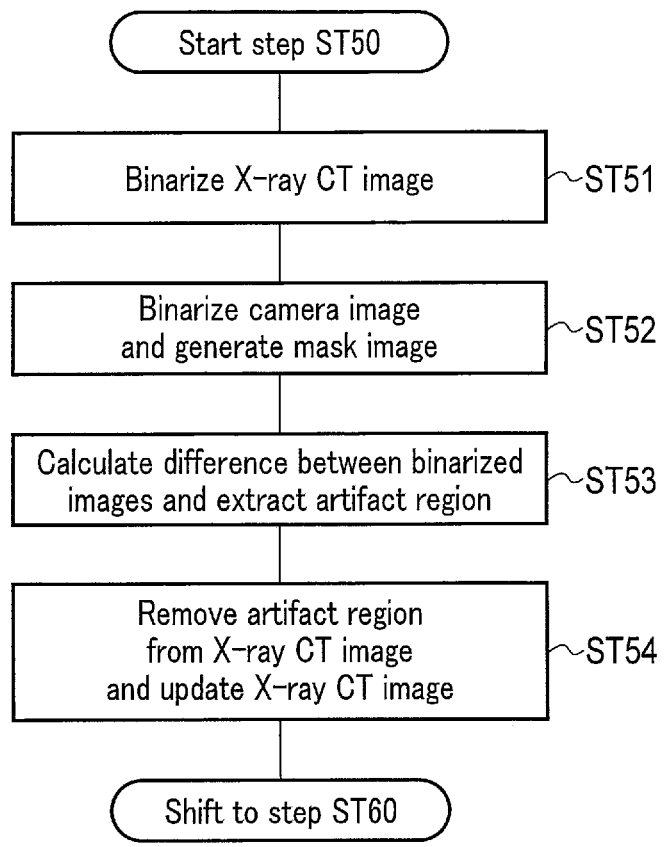
Figure 5:
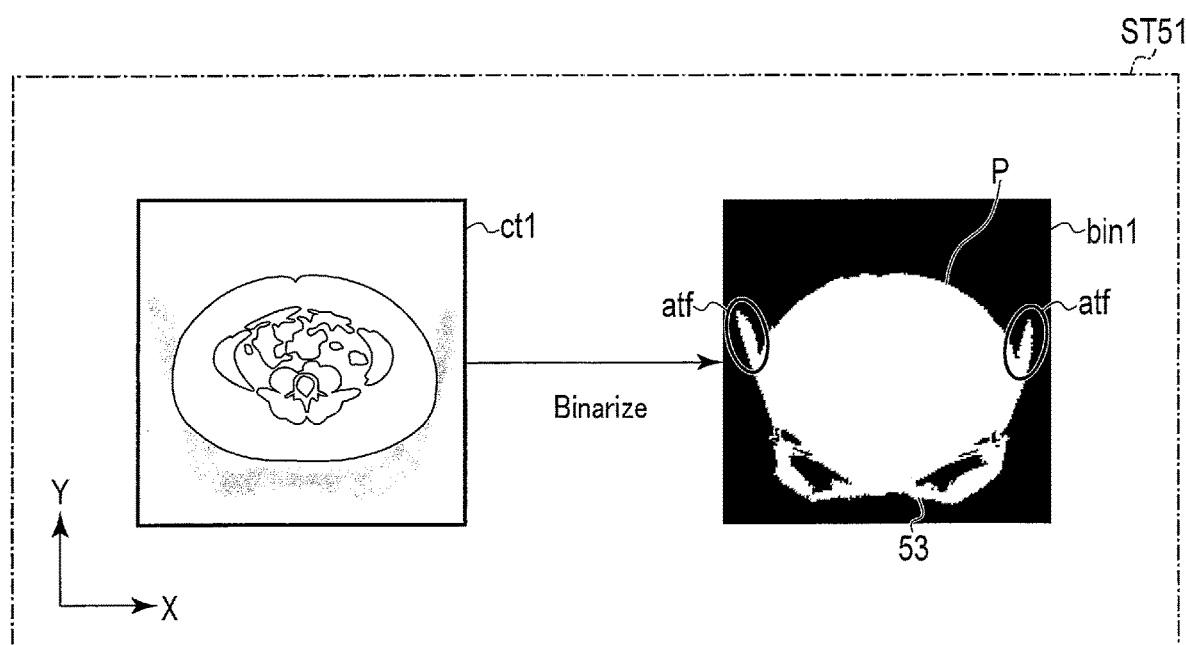
Figure 6:
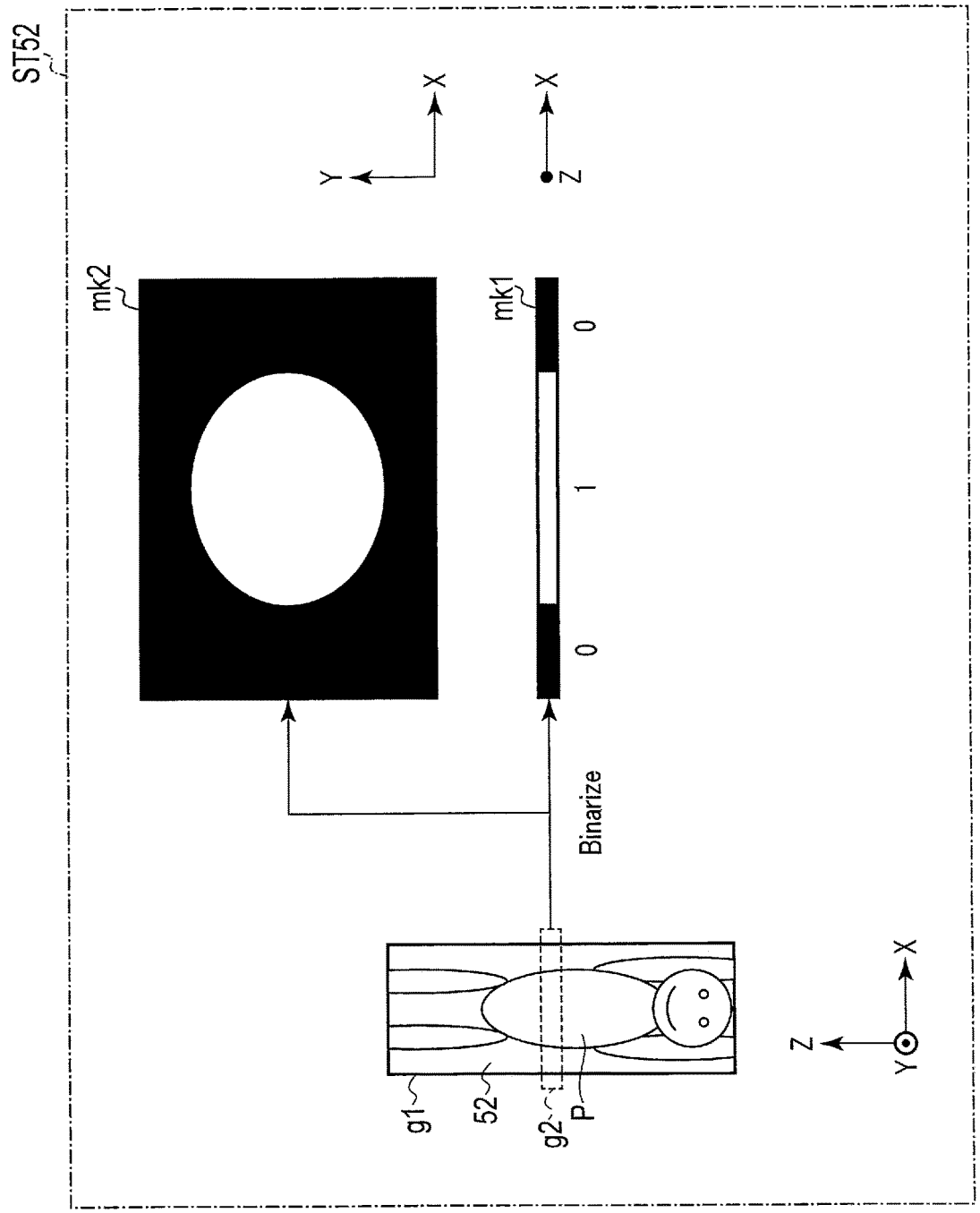
Figure 7:
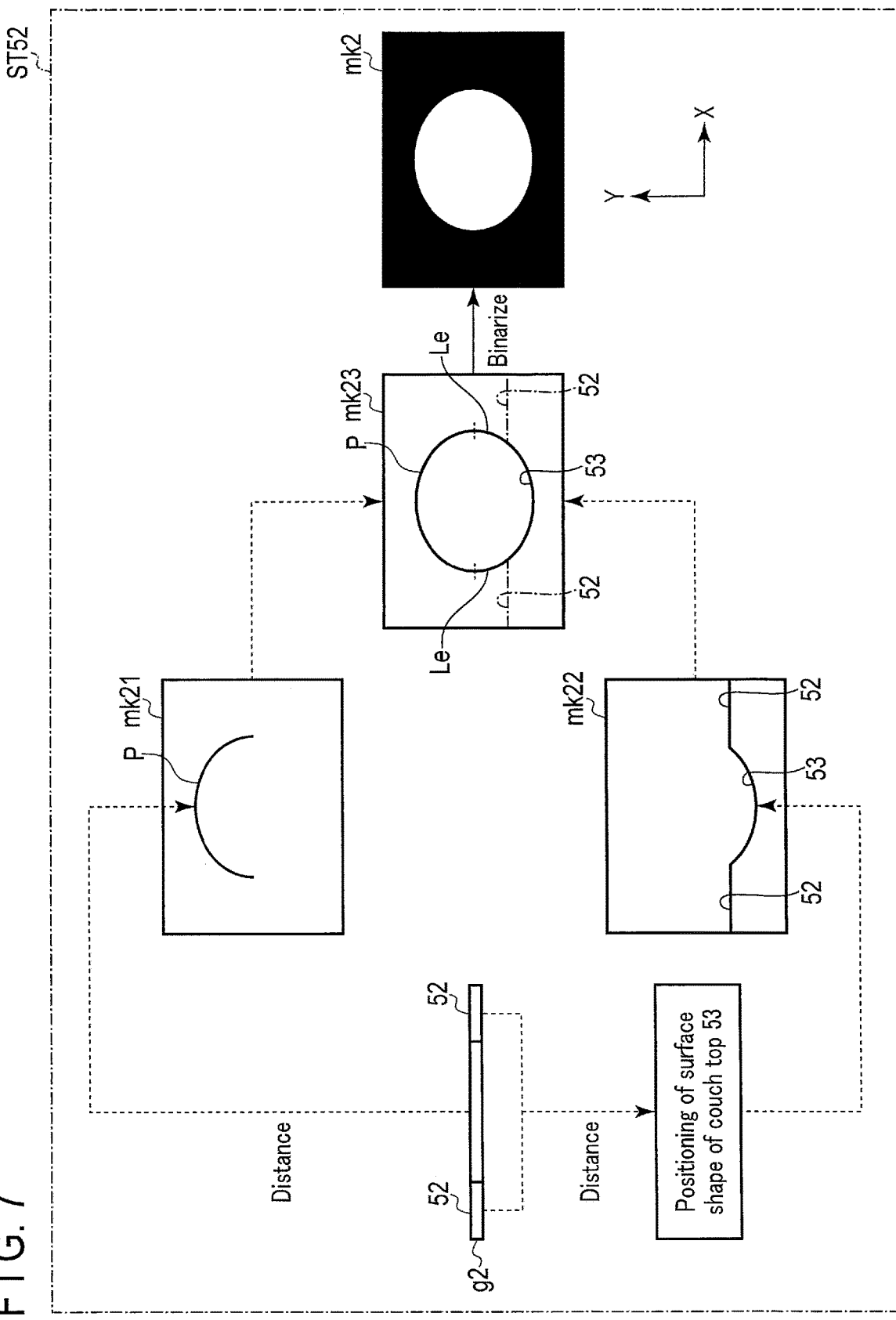
Figure 8:
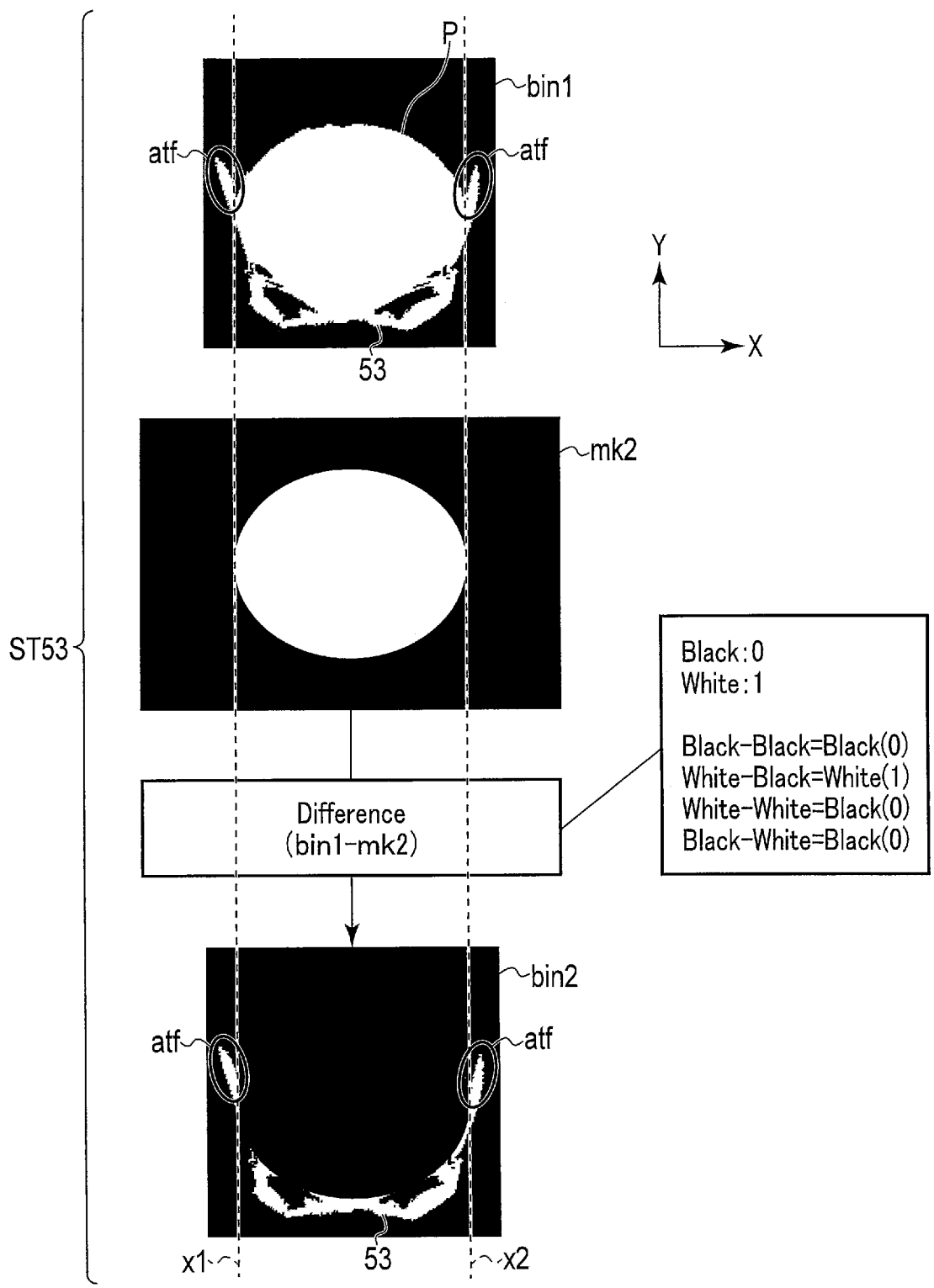
Figure 10:
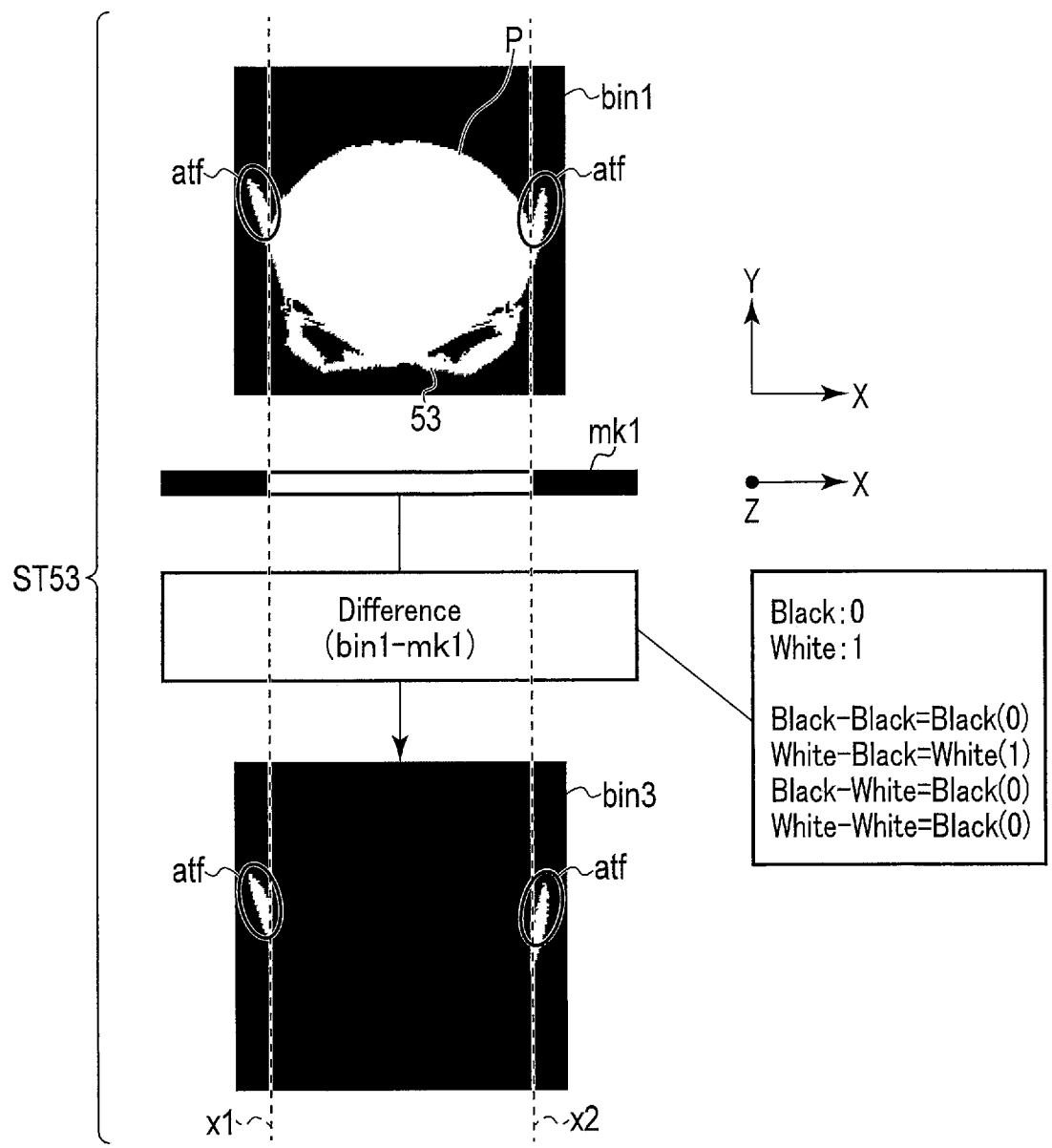
Figure 11:
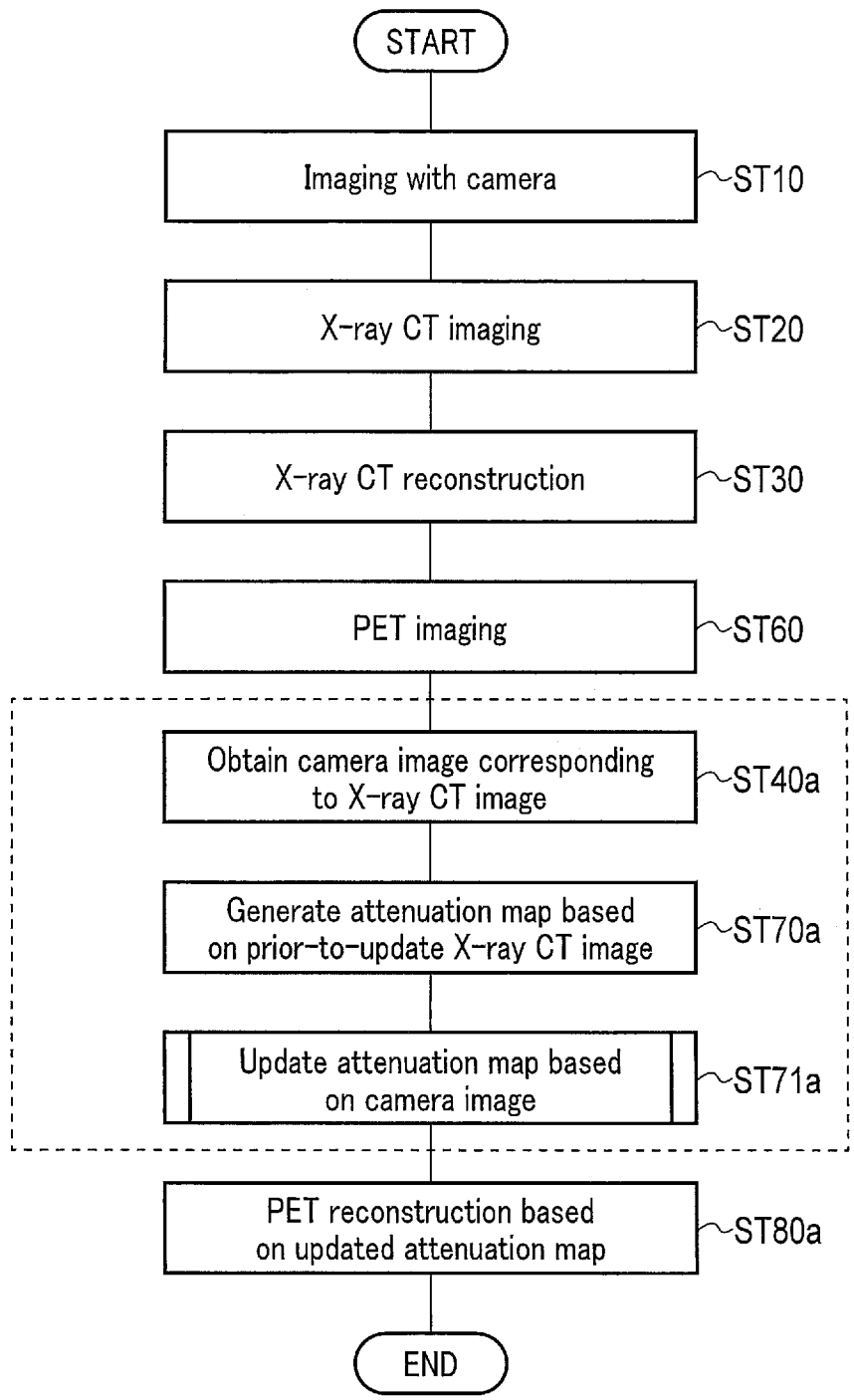
Figure 13:
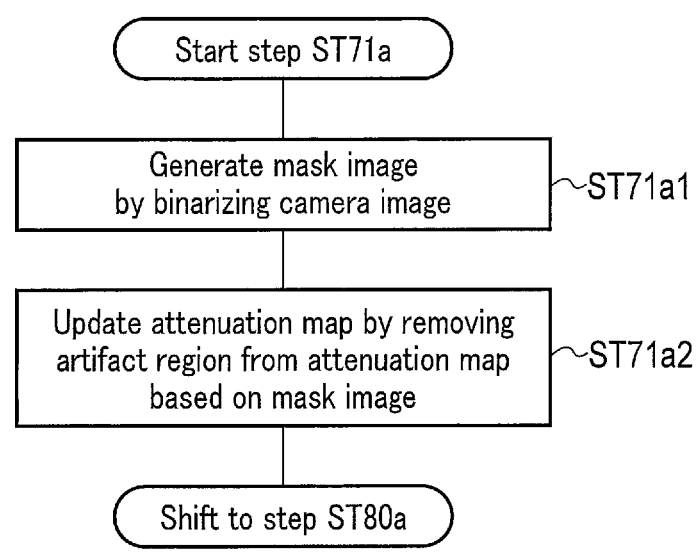
Figure 14:
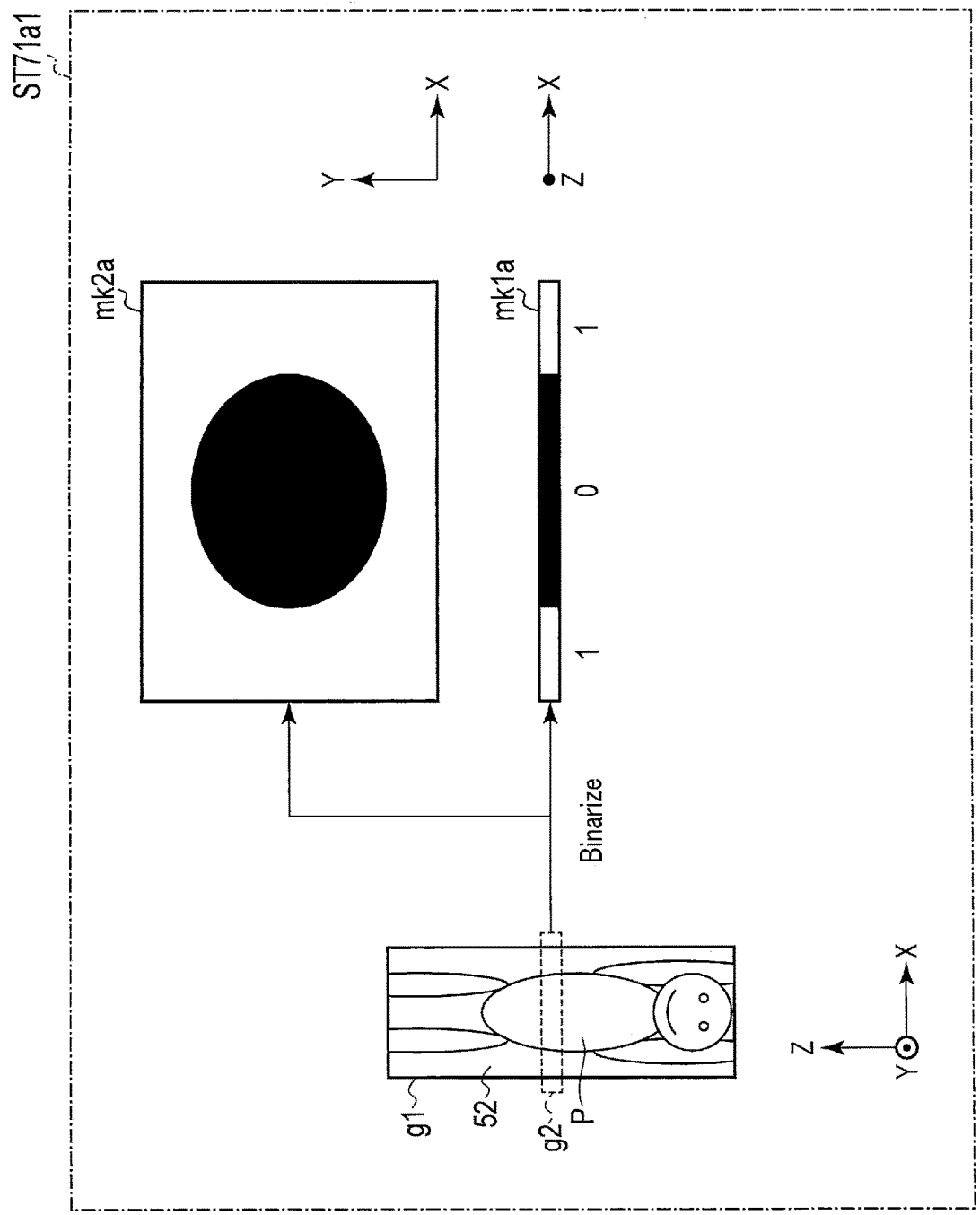
Figure 15:
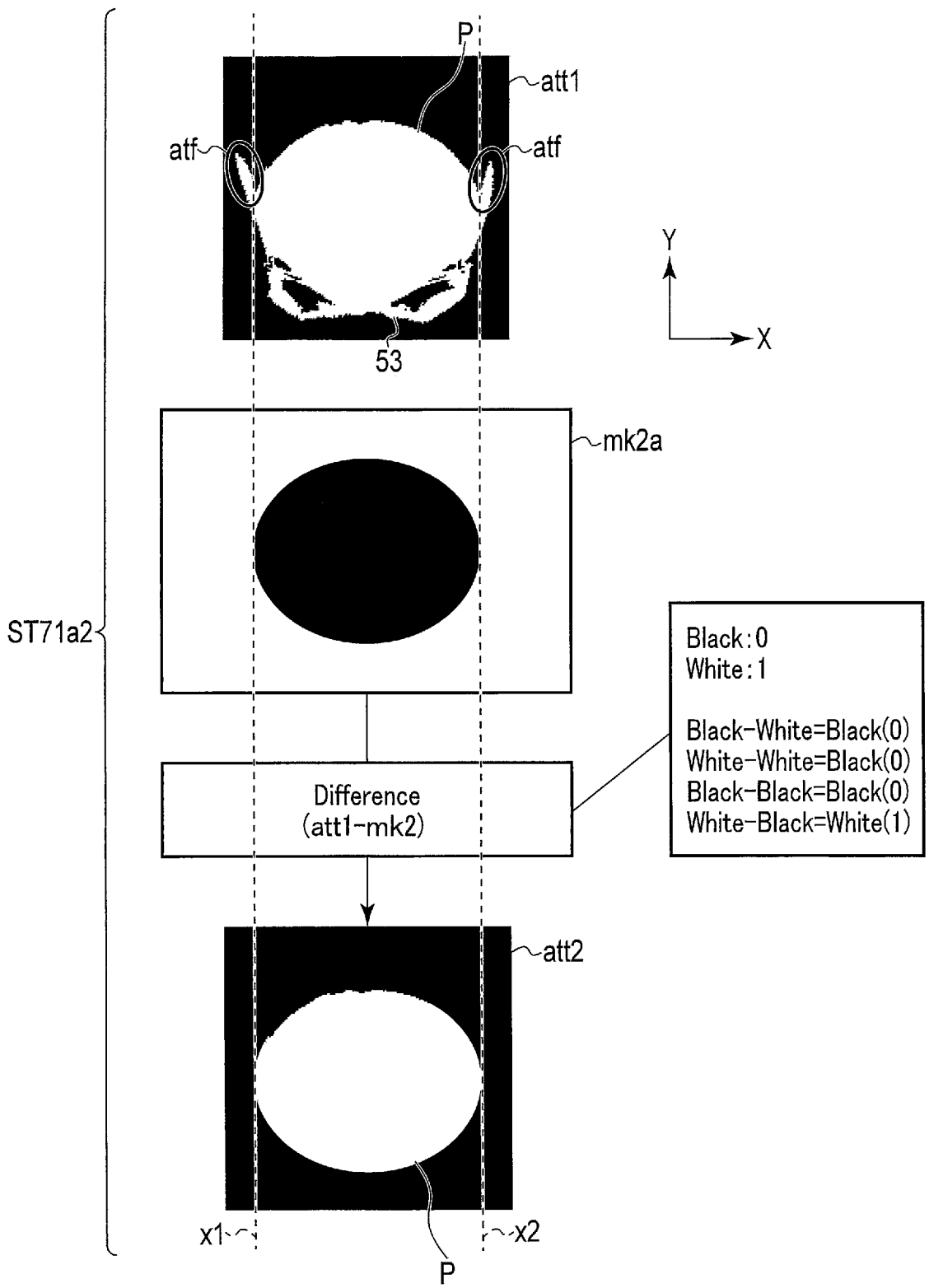
Figure 16:
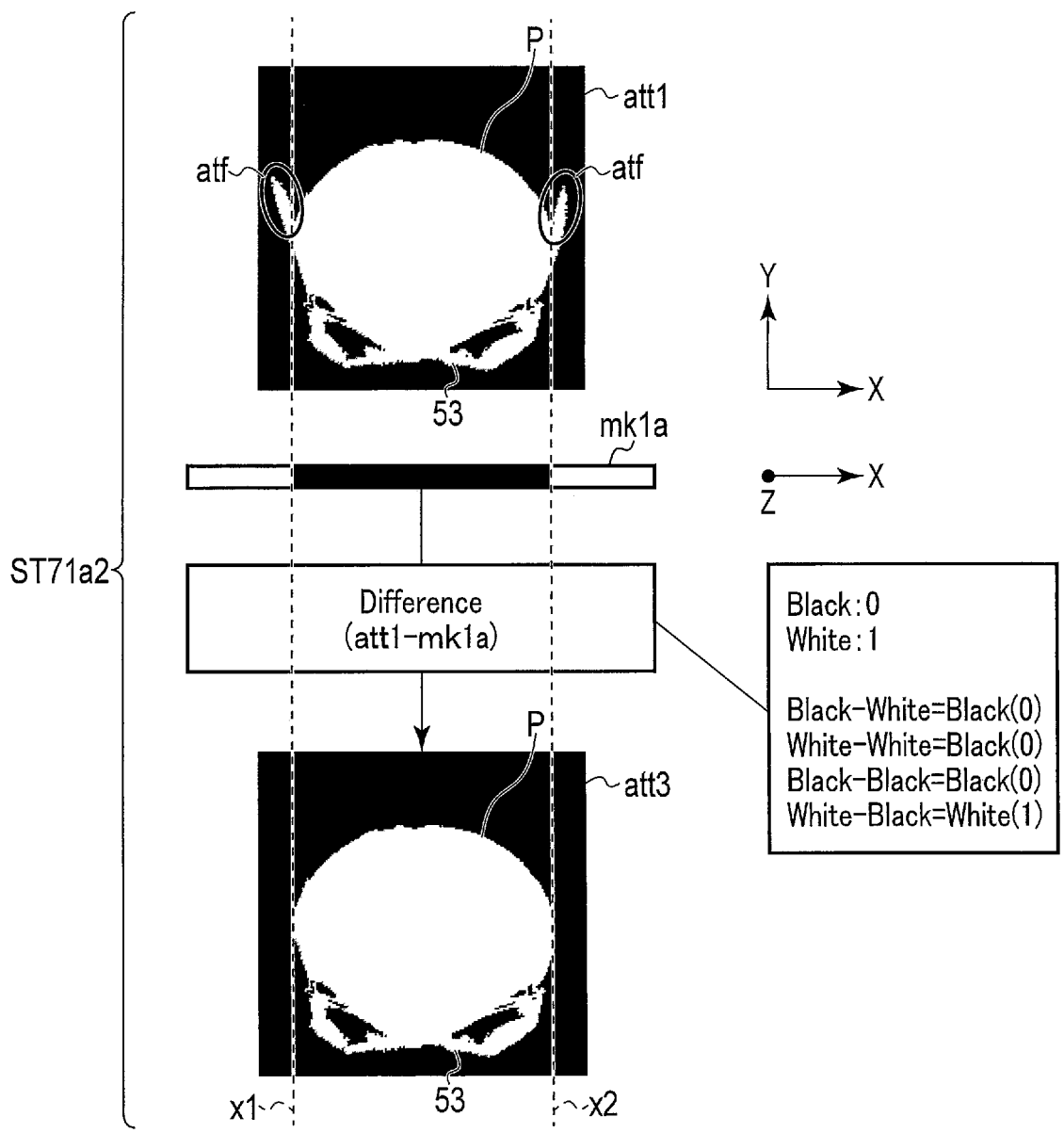
Figure 17:
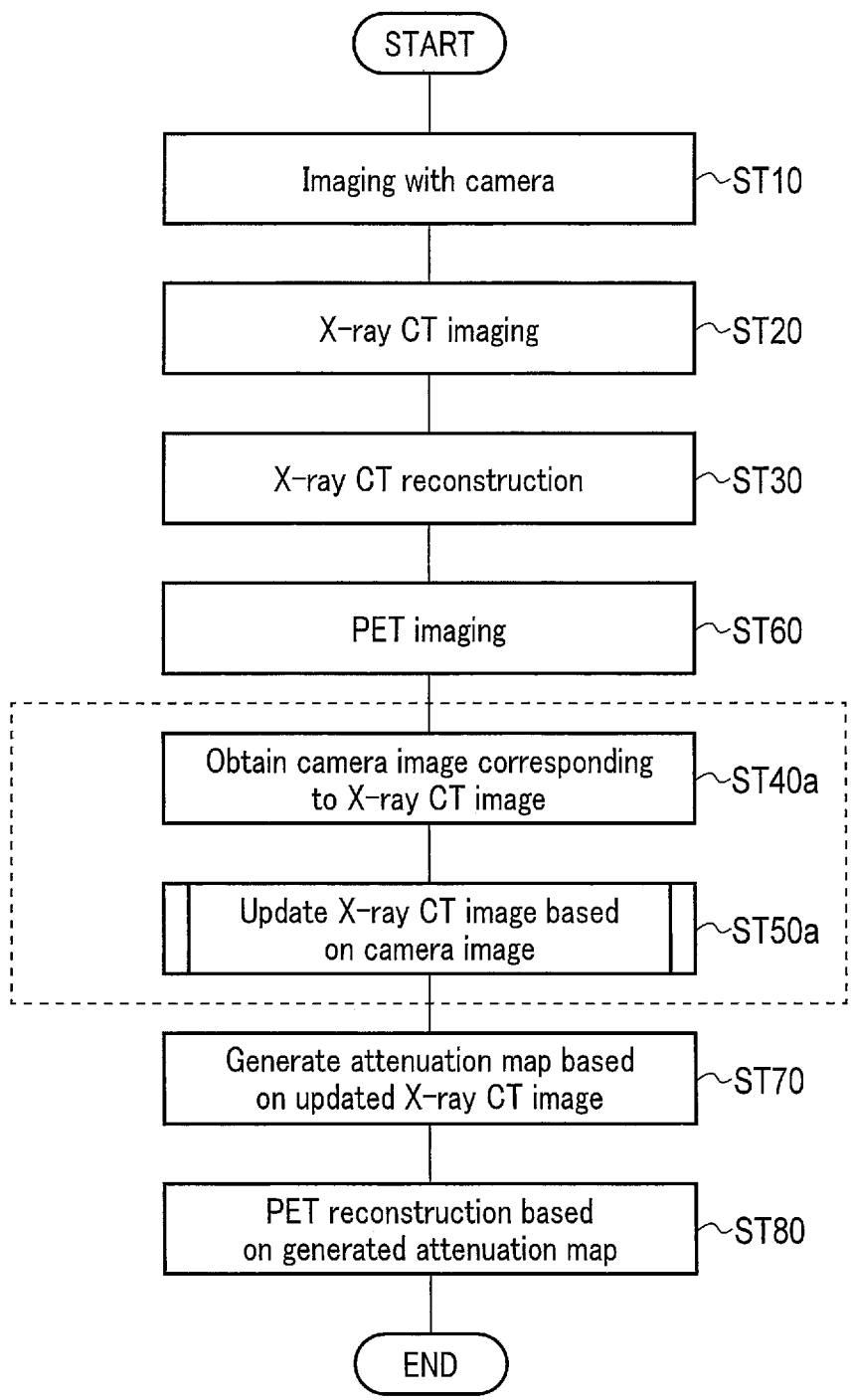
Figure 18:
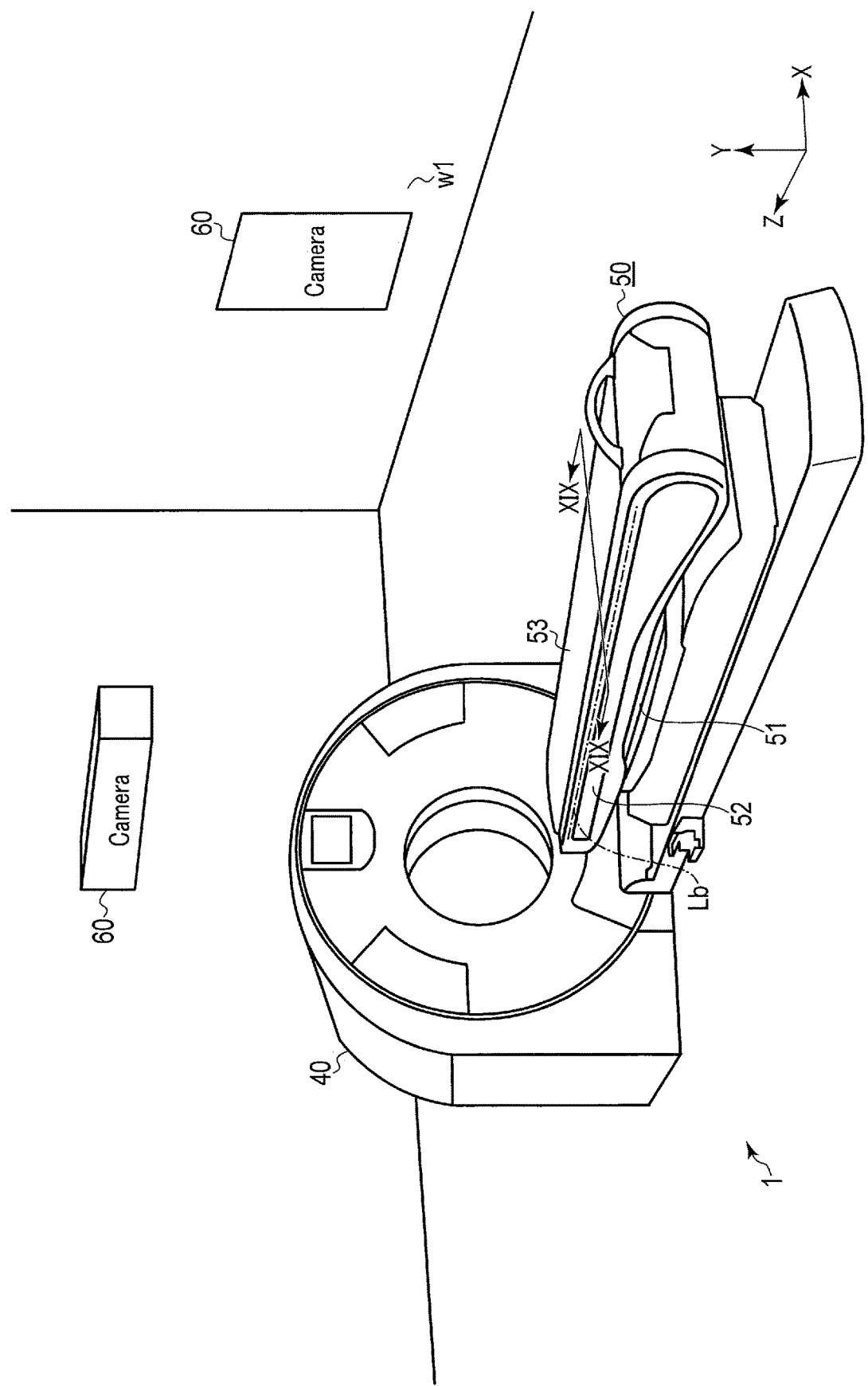
Figure 21:
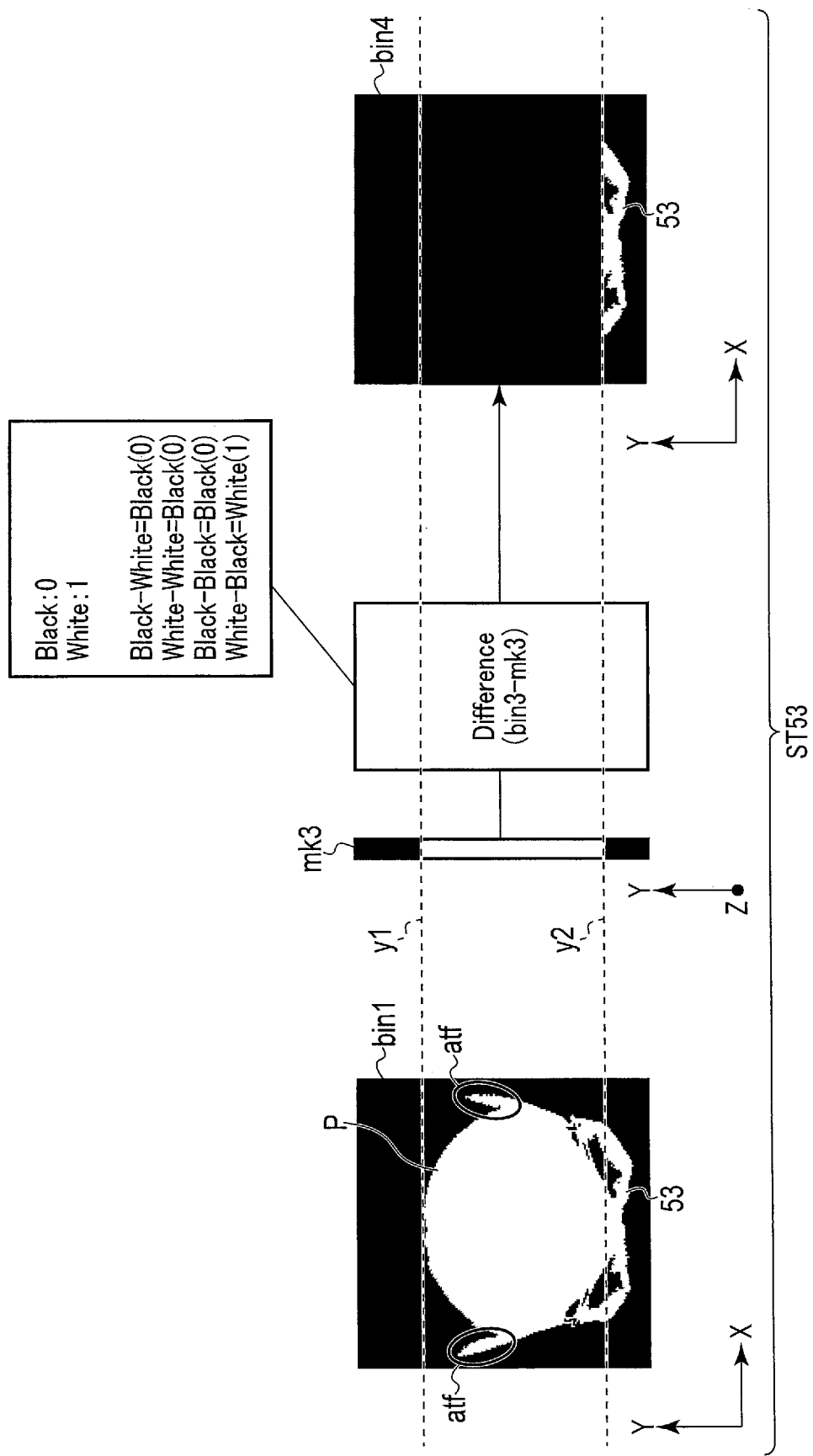
Figure 23:
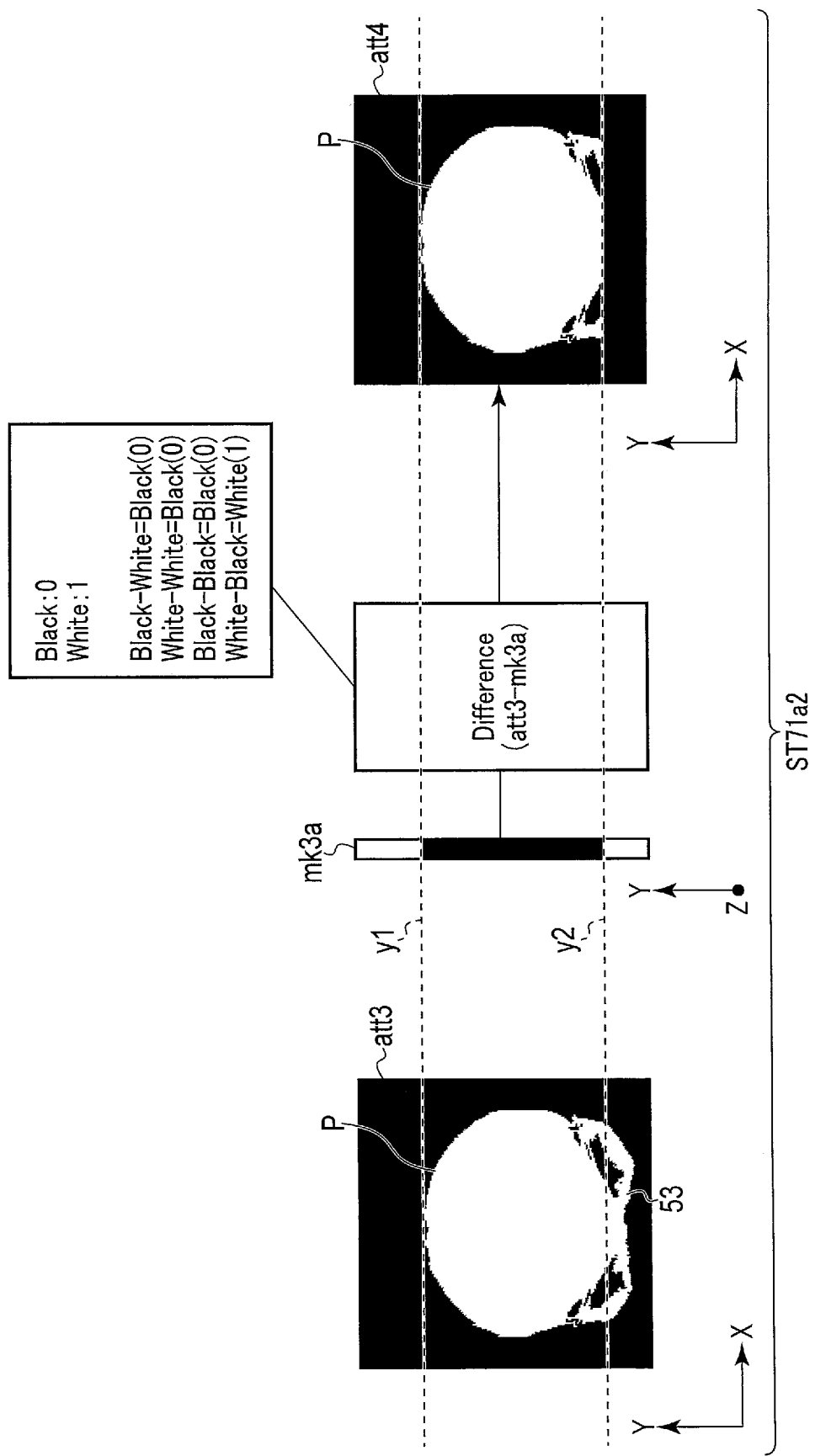
Figure 24:
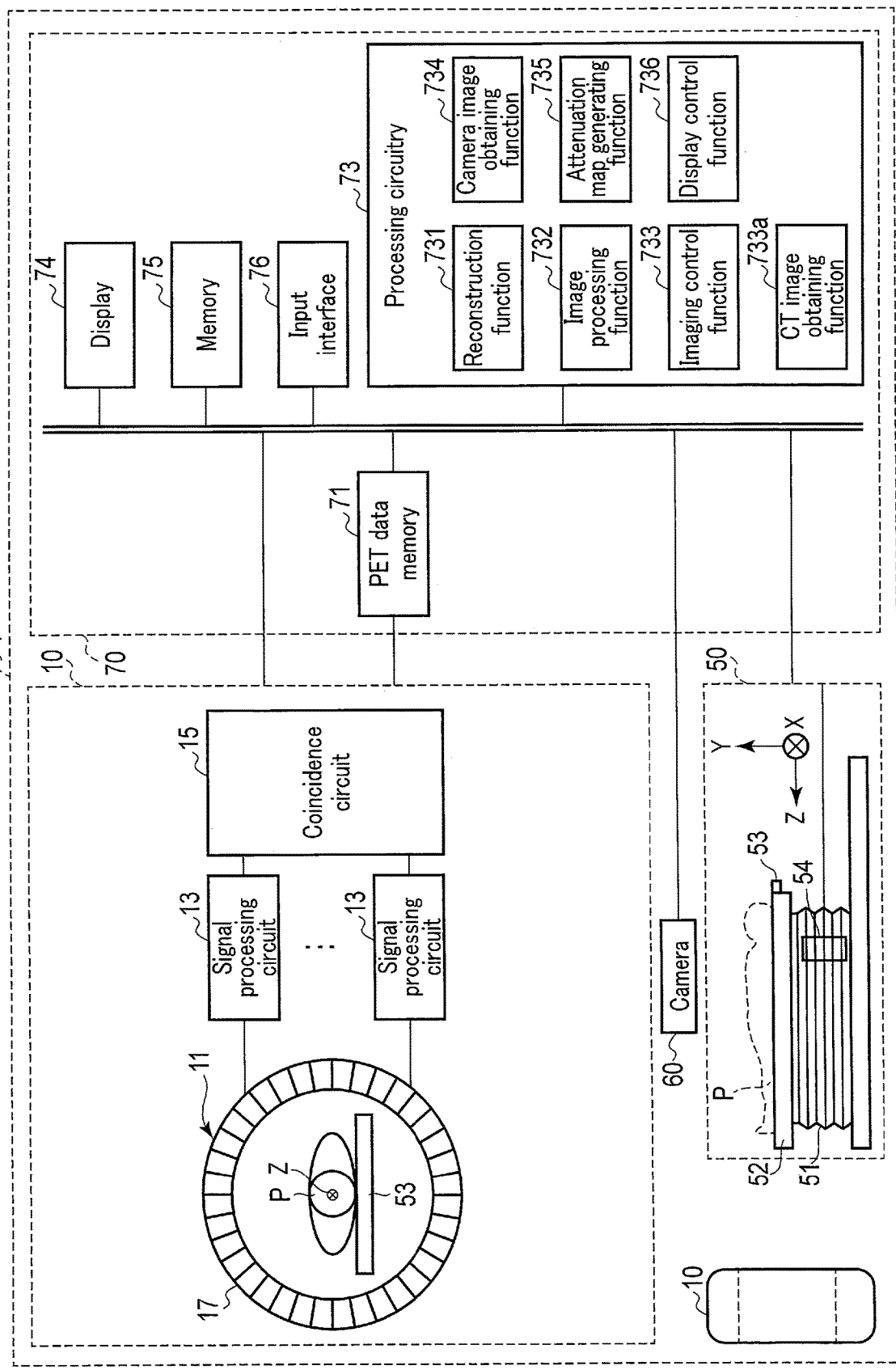

FIG. 4 is a flowchart for illustrating details of step ST50.
FIG. 5 is a schematic diagram for illustrating step ST51.
FIG. 6 is a schematic diagram for illustrating step ST52.
FIG. 7 is a schematic diagram for illustrating details of an example of step ST52.
FIG. 8 is a schematic diagram for illustrating step ST53.
FIG. 9 is a schematic diagram for illustrating step ST54.
FIG. 10 is a schematic diagram for illustrating step ST53 according to a modification of the first embodiment.
FIG. 11 is a flowchart for illustrating an example of an operation according to a second embodiment.
FIG. 12 is a schematic diagram for illustrating step ST70a.
FIG. 13 is a flowchart for illustrating details of step ST71a.
FIG. 14 is a schematic diagram for illustrating step ST71a1.
FIG. 15 is a schematic diagram for illustrating step ST71a2.
FIG. 16 is a schematic diagram for illustrating step ST71a2 according to a modification of the second embodiment.
FIG. 17 is a flowchart for illustrating an operation according to another modification of the second embodiment.
FIG. 18 is a schematic diagram showing an arrangement of a camera of a nuclear medicine diagnostic apparatus according to a modification of each embodiment.
FIG. 19 is a schematic diagram for illustrating a part of an XIX-XIX arrow cross-section in FIG. 18.
FIG. 20 is a schematic diagram for illustrating step ST52 according to a modification of the first embodiment.
FIG. 21 is a schematic diagram for illustrating step ST53 according to a modification of the first embodiment.
FIG. 22 is a schematic diagram for illustrating step ST54 according to a modification of the first embodiment.
FIG. 23 is a schematic diagram for illustrating step ST71a2 according to a modification of the second embodiment.
FIG. 24 is a diagram showing a configuration of a nuclear medicine diagnostic apparatus according to a modification of each embodiment.

DETAILED DESCRIPTION

In general, according to one embodiment, a nuclear medicine diagnostic apparatus includes processing circuitry. The processing circuitry is configured to obtain an X-ray CT image relating to a subject. The processing circuitry is configured to obtain a camera image capturing a position and a shape of the subject corresponding to the X-ray CT image. The processing circuitry is configured to generate an attenuation map based on the camera image and the X-ray CT image. The processing circuitry is configured to obtain detection data based on gamma rays radiating from a radiation source administered into the subject. The processing circuitry is configured to reconstruct an image based on the attenuation map and the detection data.

Hereinafter, embodiments will be described with reference to the drawings. In the description that follows, redundant descriptions will be omitted by assigning identical reference numerals to substantially identical parts in different drawings. Also, the nuclear medicine diagnostic apparatus according to each of the embodiments includes at least an imaging mechanism that performs PET imaging. Examples of such a medical image diagnostic apparatus include a PET apparatus equipped with only a PET imaging function, a PET/CT apparatus equipped with both a PET imaging mechanism and an X-ray CT imaging mechanism, and the like. The medical image diagnostic apparatus according to the present embodiment may be equipped with an imaging mechanism that performs at least single-photon emission CT (SPECT) imaging. Examples of such a medical image diagnostic apparatus include a SPECT apparatus equipped with only a SPECT imaging function, a SPECT/

CT apparatus equipped with both a SPECT imaging mechanism and an X-ray CT imaging mechanism, etc. The nuclear medicine diagnostic apparatus according to the present embodiment is applicable to any of these types of apparatuses; however, for concreteness it is assumed herein to be a PET/CT apparatus.

First Embodiment

Figure 1:
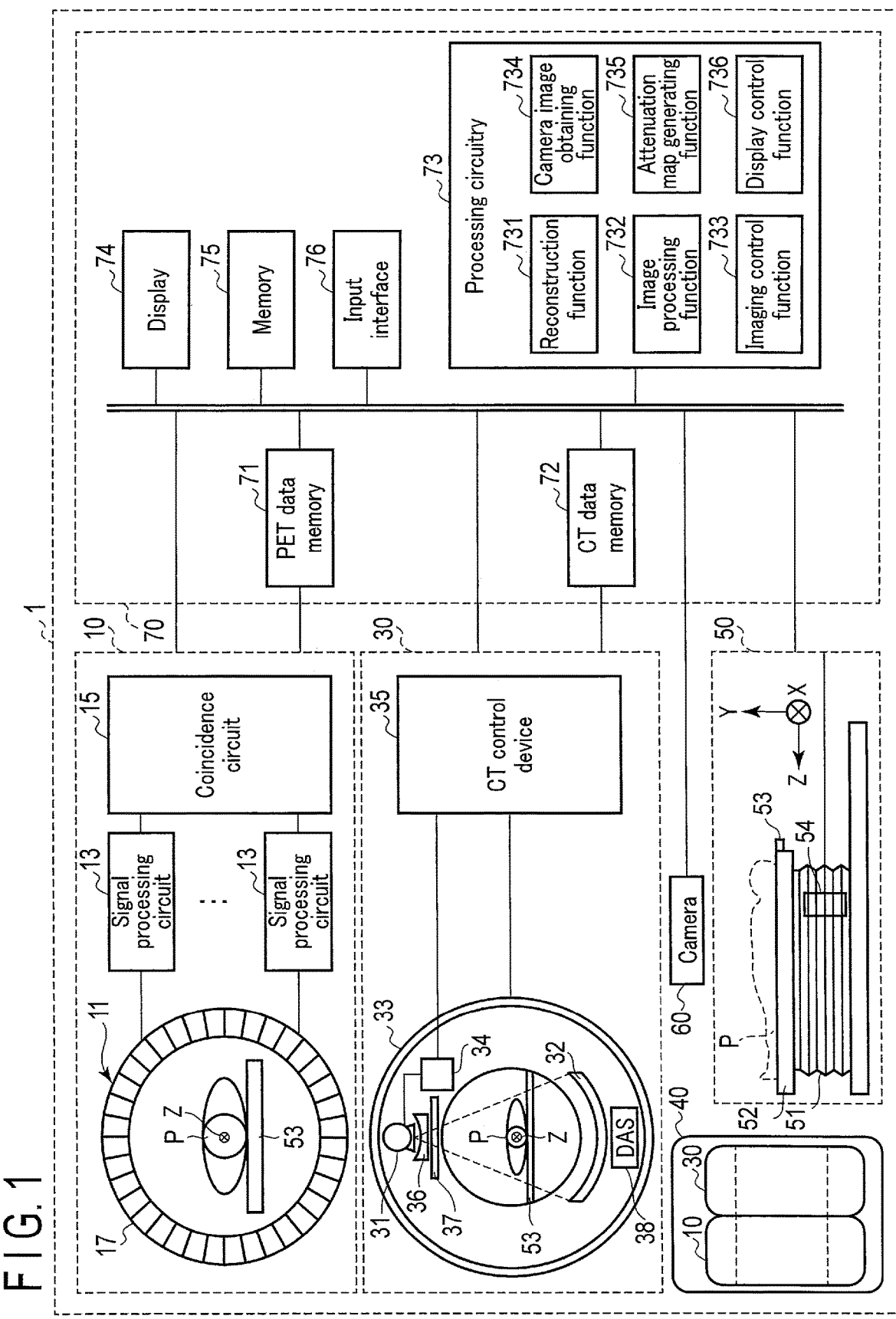
FIG. 1 is a diagram showing a configuration of a nuclear medicine diagnostic apparatus according to a first embodiment.
Figure 2:
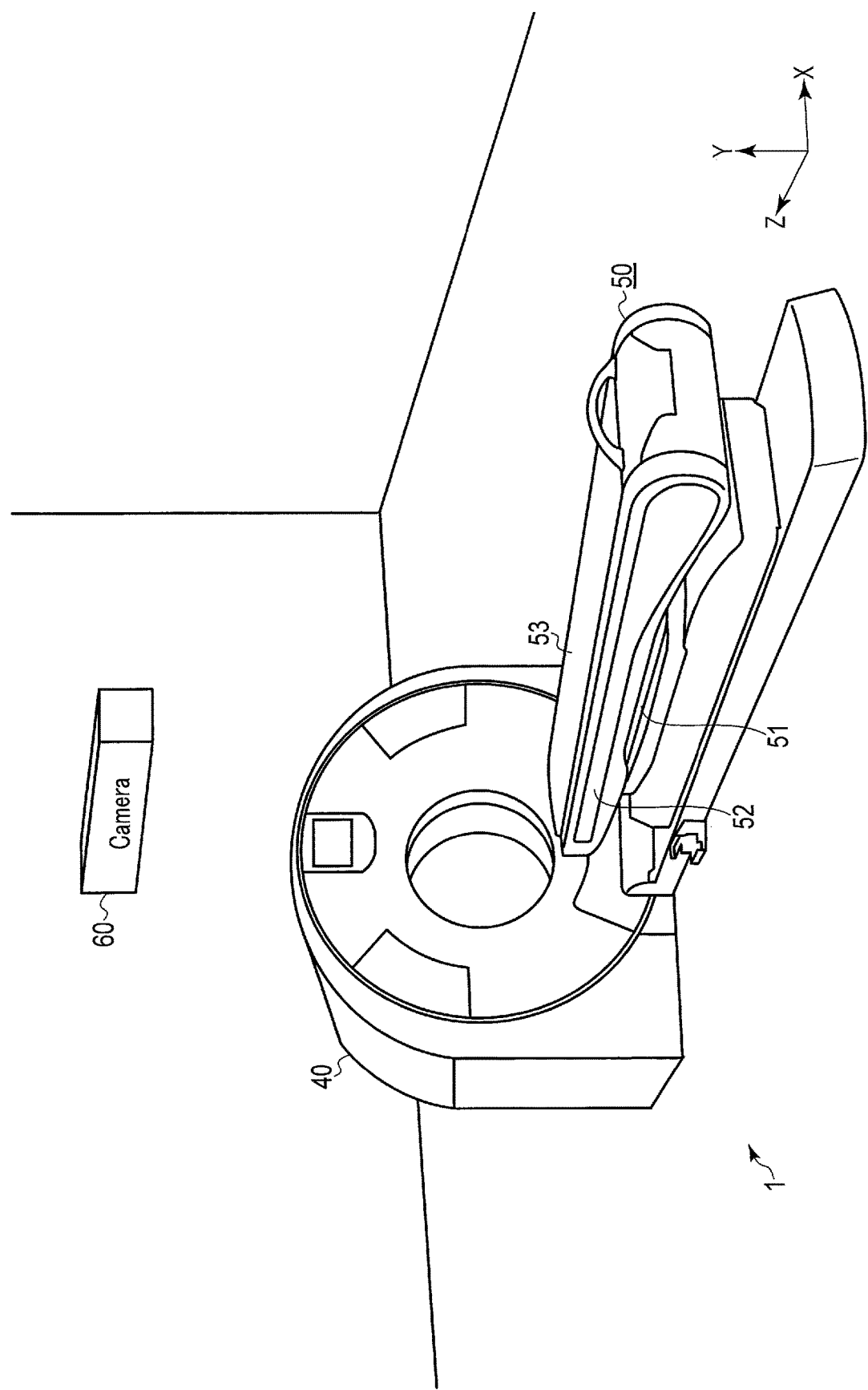
FIG. 2 is a schematic diagram showing an arrangement of a camera of the nuclear medicine diagnostic apparatus according to the first embodiment.

FIG. 1 is a diagram showing a configuration of a nuclear medicine diagnostic apparatus 1 according to a first embodiment, and FIG. 2 is a schematic diagram showing an arrangement of a camera 60 of the nuclear medicine diagnostic apparatus 1. As shown in FIGS. 1 and 2, the nuclear medicine diagnostic apparatus 1 includes a PET gantry 10, a CT gantry 30, a couch 50, a camera 60, and a console 70. The PET gantry 10 and the CT gantry 30 are integrally provided as a PET/CT gantry 40. Typically, the PET/CT gantry 40 and the couch 50 are installed in a common examination room. The camera 60 is installed on a ceiling of the examination room to image a subject P on the couch 50. However, the camera 60 is not necessarily installed on the ceiling, and may be installed on a wall of the examination room or in the PET/CT gantry 40. The console 70 is installed in a control room adjacent to the examination room. The PET gantry 10 is an imaging apparatus that performs PET imaging of the subject P. The CT gantry 30 is an imaging apparatus that images the subject P by means of X-ray CT. The couch 50 movably supports a couch top 53 on which the subject P to be imaged is mounted. The console 70 is a computer that controls the PET gantry 10, the CT gantry 30, and the couch 50.

As shown in FIG. 1, the PET gantry 10 includes a detector ring 11, a plurality of signal processing circuits 13, and a coincidence circuit 15.

The detector ring 11 includes a plurality of gamma-ray detectors 17 aligned on a circumference around a central axis Z. A field of view (FOV) is set in an opening of the detector ring 11. The subject P is positioned in such a manner that the FOV includes a site to be imaged of the subject P. A medication labeled by a positron-emitting radionuclide is administered to the subject P. A positron emitted by the positron-emitting radionuclide annihilates with a peripheral electron, and thereby a pair of annihilating gamma rays is produced. The gamma-ray detector 17 detects the pair of annihilating gamma rays emitted from a body of the subject P, and generates an electric signal corresponding to the amount of light of the detected pair of annihilating gamma rays. The gamma-ray detector 17 includes, for example, a plurality of scintillators and a plurality of photomultiplier tubes. The scintillator produces light upon receiving the pair of annihilating gamma rays derived from a radioactive isotope in the subject P. The photomultiplier tube produces an electric signal corresponding to the amount of the light. The produced electric signal is supplied to the signal processing circuits 13.

The signal processing circuits 13 generate single-event data based on the electric signal from the gamma-ray detector 17. Specifically, the signal processing circuits 13 perform a detection-time measuring process, a position calculation process, and an energy calculation process. The signal processing circuits 13 are realized by an application-specific integrated circuit (ASIC), a field-programmable gate array (FPGA), a complex programmable logic device (CPLD), or a simple programmable logic device (SPLD) configured to execute a detection-time measuring process, a position calculation process, and an energy calculation process.

In the detection-time measuring process, the signal processing circuits 13 measure a time of detection of gamma rays by the gamma-ray detector 17. Specifically, the signal processing circuits 13 monitor a peak value of an electric signal from the gamma-ray detector 17, and measure a time at which the peak value exceeds a preset threshold value as a detection time. In other words, the signal processing circuits 13 electrically detect annihilation gamma rays by detecting the peak value exceeding a threshold value. In the position calculation process, the signal processing circuits 13 calculate, based on an electric signal from the gamma-ray detector 17, a position of incidence of the pair of annihilating gamma rays. The position of incidence of the annihilation gamma rays corresponds to position coordinates of the scintillator at which the annihilation gamma rays are made incident. In the energy calculation process, the signal processing circuits 13 calculate, based on the electric signal from the gamma-ray detector 17, an energy value of the detected pair of annihilating gamma rays. Data on the detection time, data on the position coordinates, and data on the energy value relating to a single event are associated with each other. A combination of the data on the energy value, the data on the position coordinates, and the data on the detection time relating to the single event is referred to as "single-event data". The single-event data is sequentially generated every time a pair of annihilation gamma rays is detected. The generated single-event data is supplied to a coincidence circuit 15.

The coincidence circuit 15 subjects the single-event data from the signal processing circuits 13 to a coincidence process. As hardware resources, the coincidence circuit 15 is realized by an ASIC, an FPGA, a CPLD, or an SPLD configured to execute a coincidence process. In the coincidence process, the coincidence circuit 15 repeatedly specifies, from the single-event data that is supplied repeatedly, single-event data relating to two single events that fall within a predetermined time frame. It can be estimated that the pair of single events is derived from a pair of annihilating gamma rays produced from an identical annihilation point. The pair of single events is collectively referred to as a "coincidence event". A line connecting a pair of gamma-ray detectors 17 (a scintillator, more specifically) that has detected the pair of annihilating gamma rays is referred to as a line of response (LOR). The event data relating to a pair of events configuring the LOR is referred to as "coincidence-event data". The coincidence-event data and the single-event data are transmitted to the console 70. If the coincidence-event data and the single-event data are not particularly distinguished from each other, they will be referred to as "PET event data". The coincidence-event data is an example of detection data based on gamma rays radiating from a radiation source administered into the subject P. The gamma rays radiating from the radiation source administered into the subject P may be referred to as "gamma rays radiating from the subject P". Also, the radiation source may also be referred to as a "radioactive isotope". The detector ring 11, the signal processing circuits 13, and the coincidence circuit 15 are examples of an obtaining unit that obtains detection data.

In the above-described configuration, the signal processing circuits 13 and the coincidence circuit 15 are included in the PET gantry 10; however, the configuration of the present embodiment is not limited thereto. For example, the coincidence circuit 15 or both the signal processing circuits 13 and the coincidence circuit 15 may be included in an apparatus separate from the PET gantry 10. A single coincidence circuit 15 may be provided for a plurality of signal processing circuits 13 mounted on the PET gantry 10, or a plurality of coincidence circuits 15 may be respectively provided for a plurality of groups into which a plurality of signal processing circuits 13 mounted on the PET gantry 10 are divided.

As shown in FIG. 1, the CT gantry 30 includes an X-ray tube 31, an X-ray detector 32, a rotating frame 33, an X-ray high-voltage device 34, a CT control device 35, a wedge 36, a collimator 37, and a DAS 38.

The X-ray tube 31 produces X-rays. Specifically, the X-ray tube 31 includes a vacuum tube with a cathode that produces thermions and an anode that produces X-rays upon receiving the thermions liberated from the cathode. The X-ray tube 31 is connected to the X-ray high-voltage device 34 via a high-pressure cable. A tube voltage is applied across the cathode and the anode by the X-ray high-voltage device 34. Through the applying of the tube voltage, the thermions are liberated from the cathode toward the anode. Through the liberation of the thermions from the cathode toward the anode, a tube current flows. Through applying of a high voltage and supplying of a filament current by the X-ray high-voltage device 34, the thermions are liberated from the cathode toward the anode, and collide with the anode, thereby producing X-rays.

The X-ray detector 32 detects X-rays produced from the X-ray tube 31 and having passed through the subject P, and outputs an electric signal corresponding to the dose of the detected X-rays to the DAS 38. The X-ray detector 32 has a structure in which a plurality of X-ray detection element rows each including a plurality of X-ray detection elements aligned in a channel direction are aligned in a slice direction (row direction). The X-ray detector 32 is, for example, an indirect-conversion-type detector including a grid, a scintillator array, and an optical sensor array. The scintillator array includes a plurality of scintillators. The scintillators output an amount of light corresponding to a dose of incident X-rays. The grid is arranged on an X-ray incident surface side of the scintillator array, and includes an X-ray shielding plate that absorbs scattered X-rays. The optical sensor array converts the light from the scintillator into an electric signal corresponding to the amount of the light. As the optical sensor, a photodiode or a photomultiplier tube, for example, is used. The X-ray detector 32 may be a direct-conversion-type detector (semiconductor detector) including a semiconductor device that converts incident X-rays into an electric signal.

The rotating frame 33 is an annular frame that rotatably supports the X-ray tube 31 and the X-ray detector 32 about a rotation axis Z. Specifically, the rotating frame 33 supports the X-ray tube 31 and the X-ray detector 32 in such a manner that they face each other. The rotating frame 33 is rotatably supported by a fixation frame (not illustrated) around the rotation axis Z. With the rotating frame 33 being rotated around the rotation axis Z by the CT control device 35, the X-ray tube 31 and the X-ray detector 32 are rotated around the rotation axis Z. The rotating frame 33 rotates around the rotation axis Z at a given angular velocity upon receiving power from a driving mechanism of the CT control device 35. An FOV is set in an opening of the rotating frame 33.

In the present embodiment, the rotation axis of the rotating frame 33 in a non-tilted state or a longitudinal direction of the couch top 53 of the couch 50 is defined as a Z-axis direction, an axial direction orthogonal to the Z-axis direction and horizontal to the floor surface is defined as an X-axis direction, and an axial direction orthogonal to the Z-axis direction and perpendicular to the floor surface is defined as a Y-axis direction.

The X-ray high-voltage device 34 includes electric circuitry such as a transformer, a rectifier, or the like, and includes a high-voltage producing device that produces a high voltage to be applied to the X-ray tube 31 and a filament current to be supplied to the X-ray tube 31, and an X-ray control device that controls an output voltage corresponding to the X rays with which the X-ray tube 31 performs irradiation. The high-voltage producing device may be either a transformer type or an inverter type. The X-ray high-voltage device 34 may be provided in the rotating frame 33 in the CT gantry 30, or may be provided in a fixation frame (not illustrated) in the CT gantry 30.

The wedge 36 adjusts a dose of X-rays with which the subject P is irradiated. Specifically, the wedge 36 decays the X-rays in such a manner that the dose of the X-rays with which the subject P is irradiated by the X-ray tube 31 follows a predetermined distribution. As the wedge 36, for example, a metal plate of aluminum, etc., such as a wedge filter or a bow-tie filter, etc. is used.

The collimator 37 limits the irradiation range of X-rays that have passed through the wedge 36. The collimator 37 slidably supports a plurality of lead plates that shield the X-rays and adjusts the shape of slits formed by the lead plates.

The data acquisition system (DAS) 38 reads an electric signal corresponding to the dose of the X-rays detected by the X-ray detector 32 from the X-ray detector 32, amplifies the read electric signal at a variable amplification rate, and integrates the electric signal over a view period, thereby acquiring CT raw data containing a digital value corresponding to the dose of the X-rays over the view period. The DAS 38 is realized by, for example, an ASIC on which a circuit element capable of generating CT raw data is mounted. The CT raw data is transmitted to the console 70 via a non-contact data transmission device, etc.

The CT control device 35 controls the X-ray high-voltage device 34 and the DAS 38 to execute X-ray CT imaging in accordance with an imaging control function 733 of processing circuitry 73 of the console 70. The CT control device 35 includes processing circuitry including a central processing unit (CPU), etc., and a driving mechanism such as a motor, an actuator, etc. The processing circuitry includes, as hardware resources, a processor such as a CPU, a micro processing unit (MPU), etc., and a memory such as a read-only memory (ROM), a random-access memory (RAM), etc. The CT control device 35 may be realized by an ASIC, an FPGA, a CPLD, or an SPLD.

The CT gantry 30 is an example of the Rotate-Rotate type (third-generation CT), in which the X-ray tube 31 and the X-ray detector 32 integrally rotate around the subject P.

The couch 50, on which the subject P to be scanned is mounted, as shown in FIG. 1, moves the mounted subject P. The couch 50 is shared between the PET gantry 10 and the CT gantry 30.

The couch 50 includes a base 51, a supporting frame 52, a couch top 53, and a couch driving unit 54. The base 51 is installed on a floor surface. The base 51 is a housing that supports the supporting frame 52 so as to be movable in a vertical direction (Y-axis direction) with respect to the floor surface. The supporting frame 52 is a frame provided at an upper portion of the base 51. The supporting frame 52 slidably supports the couch top 53 along the central axis Z. The couch top 53 is a flexible plate on which the subject P is placed.

The couch driving unit 54 is contained in the housing of the couch 50. The couch driving unit 54 is a motor or an actuator that produces power for moving the supporting frame 52 and the couch top 53 on which the subject P is placed. The couch driving unit 54 operates under the control of the console 70, etc.

The PET gantry 10 and the CT gantry 30 are arranged in such a manner that a central axis Z of the opening of the PET gantry 10 and a central axis Z of the opening of the CT gantry 30 substantially match. The couch 50 is arranged in such a manner that a longitudinal axis of the couch top 53 becomes parallel to the central axis Z of the openings of the PET gantry 10 and the CT gantry 30. The CT gantry 30 and the PET gantry 10 are installed in this order from the side closer to the couch 50.

As shown in FIGS. 1 and 2, the camera 60 is installed on the ceiling of the examination room so as to face the couch 50. More specifically, the camera 60 is installed on the ceiling at a position above the couch 50 and the rotation axis Z, in such a manner that a direction perpendicular to the rotation axis Z becomes a direction of imaging. The position at which the camera 60 has been installed is recorded in the console 70 in advance. Accordingly, by using the position at which the camera 60 has been installed along with a distance over which the couch top 53 has been slid along the rotation axis Z, it is possible to associate positions on the rotation axis Z between an image imaged by the camera 60 and an X-ray CT image. However, the configuration is not limited thereto; for example, calibration markings may be printed on the supporting frame 52 of the couch 50, and positions between the imaged image and the X-ray CT image may be associated based on the calibration markings of the supporting frame 52 captured in the imaged image and the distance over which the couch top 53 has been slid. The camera 60 images the subject P on the couch 50, and sends the imaged image to the console 70. The imaged image is stored in a memory 75 in the console 70. As the camera 60, an optical camera, a 3D camera, an infrared camera, an ultrasonic sensor, a terahertz camera, etc., for example, can be suitably employed. If the camera 60 is a single optical camera, a single infrared camera, or a single terahertz camera, the image to be imaged will be a 2D image including a region representing a position and a shape of the subject P and an external region different from said region. If the camera 60 is an infrared camera or a terahertz camera, since an image corresponding to a body temperature of the subject P and a temperature of the external region is imaged, it is possible to suppress the effect of an examination gown on the surface of the subject compared to the optical camera. The infrared camera and the terahertz camera may be referred to as a "temperature detecting camera" or a "thermal image camera". If the camera 60 is a 3D camera or an ultrasonic camera, an image to be imaged is an image containing information on distances among the camera 60, the subject P, and the couch 50. The configuration is not limited thereto, and there may be a plurality of cameras 60. If a plurality of cameras 60 are arranged at a substantially identical position, it is preferable that different types of cameras, such as optical cameras and infrared cameras, are arranged as the cameras 60, from the viewpoint of complementing one another and improving the precision of measurement. If a plurality of cameras 60 are arranged to perform imaging in directions that are orthogonal to one another, the cameras 60 may be either of the same type or of different types. In the present embodiment, a single 3D camera is used as the camera 60.

As shown in FIG. 1, the console 70 includes a PET data memory 71, a CT data memory 72, processing circuitry 73, a display 74, a memory 75, and an input interface 76. Data communications among, for example, the PET data memory 71, the CT data memory 72, the processing circuitry 73, the display 74, the memory 75, and the input interface 76 are carried out via a bus.

The PET data memory 71 is a storage device that stores single-event data and coincidence-event data transmitted from the PET gantry 10. The PET data memory 71 is a storage device such as a hard disk drive (HDD), a solid-state drive (SSD), an integrated circuit memory device, etc.

The CT data memory 72 is a storage device that stores CT raw data transmitted from the CT gantry 30. The CT data memory 72 is a storage device such as an HDD, an SSD, an integrated circuit memory device, etc.

The processing circuitry 73 controls the entire operation of the nuclear medicine diagnostic apparatus 1 in accordance with an electric signal of an input operation output from the input interface 76. The processing circuitry 73 includes, as hardware resources, a processor such as a CPU, an MPU, a graphics processing unit (GPU), and a memory such as a ROM and a RAM. By executing various programs read from the memory, the processing circuitry 73 realizes a reconstruction function 731, an image processing function 732, an imaging control function 733, a camera image obtaining function 734, an attenuation map generating function 735, and a display control function 736. The reconstruction function 731, the image processing function 732, the imaging control function 733, the camera image obtaining function 734, the attenuation map generating function 735, and the display control function 736 may be implemented by single-board processing circuitry 73, or may be dispersively implemented by multiple-board processing circuitry 73. The various programs may include, for example, programs for realizing the functions of allowing a computer to: obtain an X-ray CT image relating to the subject P; obtain a camera image capturing a position and a shape of the subject P corresponding to the X-ray CT image; generate an attenuation map based on the camera image and the X-ray CT image; obtain detection data based on gamma rays radiating from a radiation source administered into the subject P; reconstruct an image based on the attenuation map and the detection data. Such programs may be read from the memory 75. The memory in the processing circuitry 73 and the memory 75 are examples of non-transitory computer-readable storage media.

With the reconstruction function 731, the processing circuitry 73 reconstructs an X-ray CT image representing a spatial distribution of CT values relating to the subject P, based on the CT raw data transmitted from the CT gantry 30. As the image reconstruction algorithm, existing image reconstruction algorithms such as filtered back projection (FBP) and successive-approximation reconstruction can be used. In addition thereto, extended reconstruction technology, in which a range of reconstruction is extended by inferring a missing portion of a partially missing sinogram, is used. The processing circuitry 73 reconstructs a PET image showing a distribution of the positron-emitting radionuclide administered into the subject P, based on the coincidence-event data transmitted from the PET gantry 10 and the attenuation map generated by the attenuation map generating function 735. Also, the processing circuitry 73 can generate a positioning image relating to PET imaging based on PET event data, or generate a positioning image relating to X-ray CT imaging based on CT raw data. It is to be noted that the CT gantry 30, the reconstruction function 731, and the processing circuitry 73 are examples of a CT image obtaining unit that obtains X-ray CT images relating to a subject P. The reconstruction function 731 and the processing circuitry 73 are examples of a reconstruction unit that reconstructs an image (nuclear medicine image) based on the attenuation map and the detection data. The PET image is an example of an image to be reconstructed.

With the image processing function 732, the processing circuitry 73 subjects the PET image and the X-ray CT image reconstructed by the reconstruction function 731 to a variety of image processing. For example, the processing circuitry 73 converts X-ray CT image data generated by the reconstruction function 731 to tomographic image data in a given cross section or three-dimensional image data (volume data) by a publicly known method, based on an input operation made by an operator via the input interface 76. The volume data is data containing distribution information of CT values in a three-dimensional space. It is to be noted that the three-dimensional image data may be generated directly by the reconstruction function 731. The processing circuitry 73 generates a display image by, for example, subjecting the PET image and the X-ray CT image to three-dimensional image processing such as volume rendering, surface volume rendering, voxel-value projection, multiplanar reconstruction (MPR), curved MPR (CPR), etc.

With the imaging control function 733, the processing circuitry 73 synchronously controls the PET gantry 10 and the couch 50 to perform PET imaging. It is assumed that the PET imaging according to the present embodiment is intermittent-move scanning ("step and shoot"), by which PET event data is acquired for every acquisition area while the couch top 53 is intermittently moved. Also, the processing circuitry 73 synchronously controls the CT gantry 30 and the couch 50 to perform X-ray CT imaging. In the case of continuously performing PET imaging and X-ray CT imaging, the PET gantry 10, the CT gantry 30, and the couch 50 are synchronously controlled. Also, the processing circuitry 73 is capable of executing positioning scanning with the PET gantry 10 (hereinafter referred to as "PET positioning scanning") and positioning scanning with the CT gantry 30 (hereinafter referred to as "CT positioning scanning"). For the PET positioning scanning, the processing circuitry 73 synchronously controls the PET gantry 10 and the couch 50. For the CT positioning scanning, the processing circuitry 73 synchronously controls the CT gantry 30 and the couch 50.

With the camera image obtaining function 734, the processing circuitry 73 obtains a camera image capturing a position and a shape of the subject P corresponding to the X-ray CT image. The camera image is acquired by cutting a portion of an imaged image in the memory 75 at a position (a position on the Z axis) corresponding to that in the X-ray CT image. Such a camera image is obtained with the camera image obtaining function 734 from an image imaged by the camera 60, which is at least one optical camera, 3D camera, infrared camera, ultrasonic sensor, or terahertz camera. The camera image obtaining function 734 and the processing circuitry 73 are examples of a camera image obtaining unit.

With the attenuation map generating function 735, the processing circuitry 73 generates an attenuation map based on the camera image obtained by the camera image obtaining function 734 and the X-ray CT image reconstructed by the reconstruction function 731. For example, the processing circuitry 73 may update the X-ray CT image to remove, from the X-ray CT image, an artifact region different from a region of the subject P based on the camera image, and generate an attenuation map based on the updated X-ray CT image. In this case, the attenuation map generating function 735 may include functions <i> to <iv> listed below. Either of the functions <i> and <ii> may be executed first.

<i> A process of generating a first binary image by binarizing an X-ray CT image according to whether or not each pixel configuring the X-ray CT image falls in a region relating to the subject P. It is to be noted that the first binary image may be a first attenuation map generated from the X-ray CT image.

<ii> A process of generating a mask image by binarizing a camera image according to whether or not each pixel configuring the camera image falls in a region of the subject P. It is to be noted that the mask image may be referred to as "subject structure information" indicating whether or not each pixel falls in the region of the subject P.

<iii> A process of generating, based on the mask image, a second binary image in which an artifact region different from the region of the subject P is extracted from the region relating to the subject P included in the first binary image.

<iv> A process of updating the X-ray CT image to remove, from the X-ray CT image, a region corresponding to the artifact region in the second binary image, based on the second binary image. In the case of removing, from the X-ray CT image, the region corresponding to the artifact region in the second binary image, the attenuation map generating function 735 sets the voxel value of the region to be removed from the X-ray CT image to be −1000 Hounsfield units (HU), which is the value of air.

It is to be noted that the above-described extracted and removed "artifact region" is so called since artifacts tend to be caused by extended reconstruction in such a region, which is different from the region of the subject P, and corresponds to a region outside the FOV of the CT gantry 30. It is to be added that the above-described extracted and removed artifact region is not necessarily a region in the X-ray CT image in which artifacts actually exist. Accordingly, the term "artifact region" may be replaced with other terms such as "deemed artifact region", "outside region", or "extended field-of-view region".

With the display control function 736, the processing circuitry 73 displays a variety of information on the display 74. The processing circuitry 73 displays, for example, a PET image and an X-ray CT image reconstructed by the reconstruction function 731. Also, the processing circuitry 73 may display, for example, an X-ray CT image updated by the attenuation map generating function 735. Also, the processing circuitry 73 may display, for example, an imaged image in the memory 75, and display a camera image obtained by the camera image obtaining function 734.

The display 74 displays a variety of information under the control of the processing circuitry 73 with the display control function 736. For the display 74, a CRT (cathode-ray tube) display, a liquid crystal display, an organic electroluminescence (EL) display, a light-emitting diode (LED) display, a plasma display, or any other displays known in the present technical field, for example, may be suitably employed.

The memory 75 is a storage device configured to store a variety of information, such as an HDD, an SSD, an integrated circuit memory device, etc. The memory 75 may also be a drive, etc. configured to read and write a variety of information to and from a compact disc read-only memory (CD-ROM) drive, a Digital Versatile Disc (DVD) drive, a portable storage medium such as a flash memory, etc. The memory 75 stores, for example, imaged images sent from the camera 60.

The input interface 76 inputs various instructions from the user. Specifically, the input interface 76 is connected to an input device. Examples of the input device that may be employed include: a keyboard, a mouse, a trackball, a joystick, a touchpad, a touchscreen in which a display screen and a touch pad are made integral, non-contact input circuity using an optical sensor, speech input circuitry, various switches, etc. The input interface 76 supplies an output signal from the input device to the processing circuitry 73 via a bus. Herein, the input interface 76 does not necessarily include a physical operational component, such as a mouse, a keyboard, etc. For example, electric signal processing circuitry that receives an electric signal corresponding to an input operation from an external input device provided separately from the apparatus and outputs the electric signal to the processing circuitry 73 is included in the examples of the input interface 76.

Next, an operation of the nuclear medicine diagnostic apparatus 1 with the above-described configuration will be described using the flowcharts shown in FIGS. 3 and 4 and the schematic diagrams shown in FIGS. 5 to 9. In the description that follows, a flow of a PET/CT examination will be discussed. It is assumed that the PET/CT examination refers to a medical examination that performs both PET imaging and X-ray CT imaging.

Figure 3:
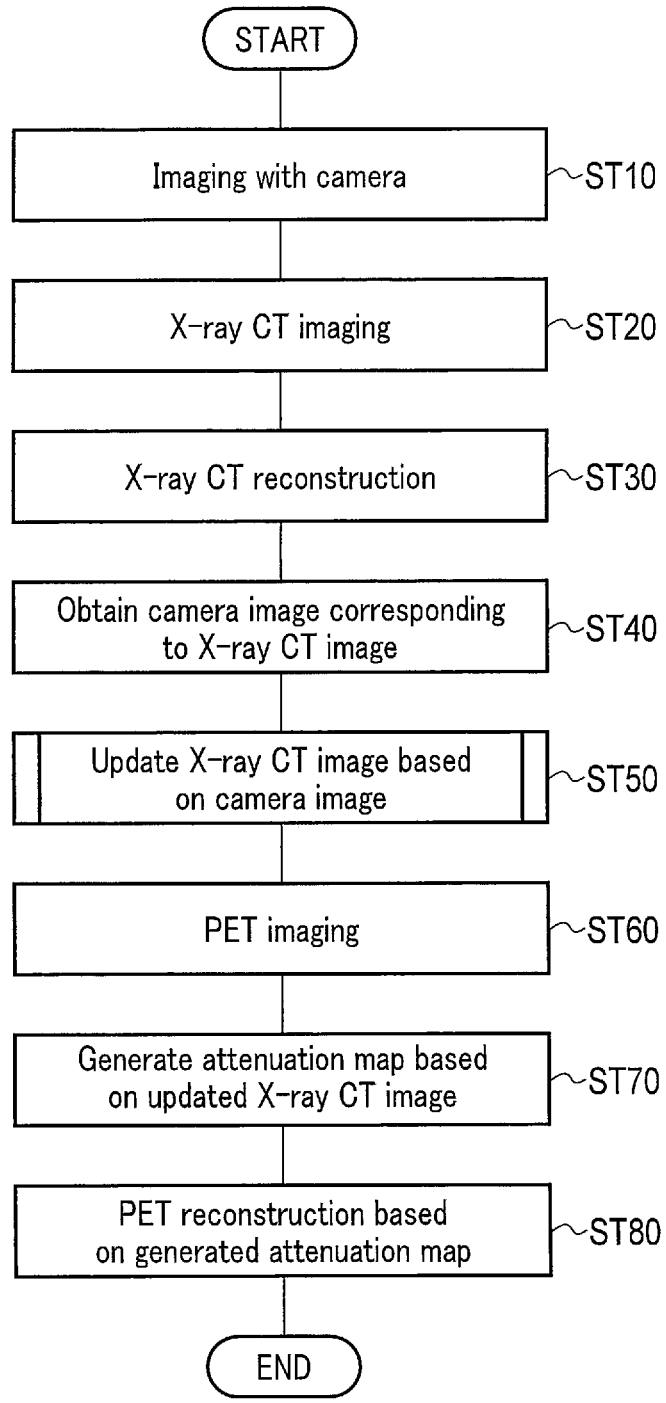
FIG. 3 is a flowchart for illustrating an example of an operation in the first embodiment.

As shown in FIG. 3, at step ST10, the camera 60 images the subject P on the couch top 53 supported by the supporting frame 52 in accordance with, for example, an operation on an operation panel provided in the PET/CT gantry 40, and sends an imaged image to the console 70. In the imaged image, the supporting frame 52 is shown on both sides of the subject P lying on his or her back. It is to be noted that the couch top 53 is, for example, hidden by the subject P and not shown in the imaged image. However, the configuration is not limited thereto, and the couch top 53 and the supporting frame 52 may be shown in this order on both sides of the subject P in the imaged image.

After step ST10, at step ST20, the processing circuitry 73 synchronously controls the CT gantry 30 and the couch 50, and allows the CT gantry 30 to perform CT positioning scanning. The CT positioning scanning is X-ray CT imaging for acquiring an image of the entire body of the subject P supplied for confirmation, setting, etc. of the imaging range. As the CT positioning scanning, scanography and helical scanning are applicable. Scanography is performed by performing X-ray irradiation with the X-ray tube 31 and X-ray detection with the X-ray detector 32 with the rotation angle of the X-ray tube 31 and the X-ray detector 32 being fixed, while sliding the couch top 53. The rotation angles of the X-ray tube 31 and the X-ray detector 32 are typically fixed to the front direction or the side direction of the subject P. The helical scanning is performed by sliding the couch top 53, while performing X-ray irradiation with the X-ray tube 31 and X-ray detection with the X-ray detector 32, with the X-ray tube 31 and the X-ray detector 32 rotating at a high speed.

The processing circuitry 73 generates a CT positioning image based on CT raw data acquired by positioning scanning, and causes the display 74 to display the CT positioning image. This allows the user to confirm the positional relationship between the PET image acquisition area and the subject P in more detail, and to make minor adjustments to the acquisition area, where necessary.

Thereafter, the processing circuitry 73 synchronously controls the CT gantry 30 and the couch 50, and allows the CT gantry 30 to perform CT imaging.

After step ST20, at step ST30, the processing circuitry 73 reconstructs an X-ray CT image based on CT raw data acquired by the X-ray CT imaging. In this reconstruction, extended reconstruction technology, by which a range of reconstruction is extended by inferring a missing portion of a partially missing sinogram, is used. However, in accordance with the extended reconstruction, the X-ray CT image includes, in the periphery of the region of the subject P, an artifact region in which artifacts tend to be caused. Through steps ST20 to ST30, the processing circuitry 73 obtains the X-ray CT image relating to the subject P.

After step ST30, at step ST40, the processing circuitry 73 obtains a camera image capturing the position and the shape of the subject P corresponding to the X-ray CT image. The processing circuitry 73 obtains the camera image by, for example, cutting a portion of an imaged image in the memory 75 at a position corresponding to that in the X-ray CT image.

After step ST40, at step ST50, the processing circuitry 73 updates the X-ray CT image to remove, from the X-ray CT image, an artifact region different from the region of the subject P, based on the obtained camera image. Step ST50 is executed by steps ST51 to ST54 as shown in FIGS. 4 to 9.

At step ST51, as shown in FIGS. 4 and 5, the processing circuitry 73 generates a first binary image bin1 by binarizing an X-ray CT image ct1 according to whether or not each pixel falls in a region relating to the subject P. The first binary image bin1 represents the region relating to the subject P in the X-ray CT image ct1 as "1", and represents a region different from the region relating to the subject P as "0". The first binary image bin1 may be a first attenuation map generated from the X-ray CT image ct1. In FIG. 5, the first binary image bin1 includes, as the region relating to the subject P, a region representing the subject P, artifacts atf, and the couch top 53. It is to be added that, in the first binary image bin1, a substantially oval region of the subject P exists at an approximate center, a region of artifacts atf exists on right and left sides of the subject P, and a region of the couch top 53 exists below the subject P. The supporting frame 52 that supports the couch top 53 is not slid into the PET/CT gantry 40, and is therefore not shown in the X-ray CT image ct1 and the first binary image bin1.

After step ST51, at step ST52, as shown in FIGS. 4 and 6, the processing circuitry 73 generates a mask image mk1 or a mask image mk2 by binarizing a camera image g2 obtained from an imaged image g1 according to whether or not each pixel falls in the region of the subject P. The mask images mk1 and mk2 represent the region of the subject P in the camera image g2 as "1", and represents an artifact region different from the region of the subject P as "0". The mask image mk1 is an example of the case where the imaged image g1 and the camera image g2 are two-dimensional images.

On the other hand, the mask image mk2 is a binarized image generated based on the camera image g2 in the case where the imaged image g1 and the camera image g2 contain distance information. The camera image g2 further captures the couch 50 on which the subject P is placed. In this case, the processing circuitry 73 detects, based on, for example, the couch 50 in the camera image g2 and preset information relating to the shape of the couch 50, a boundary between the subject P and the couch 50, and generates a mask image mk2 by regarding a side opposite to the subject P relative to the boundary as a part of a region different from the subject P. Specifically, as shown in FIG. 7, for example, the processing circuitry 73 generates, based on the region of the subject P positioned at the center of the camera image g2, an image mk21 including a curve associated with a distance from the camera 60 to the subject P. The processing circuitry 73 performs positioning of the surface shapes of the supporting frame 52 and the couch top 53 in accordance with a distance from the camera 60 to the supporting frame 52 based on the region of the supporting frame 52 positioned at both ends of the camera image g2. The data on the surface shape of the supporting frame 52 and the couch top 53 is stored in advance in the memory 75. The data on the surface shape of the supporting frame 52 and the couch top 53 is an example of information relating to the shape of the couch 50. Thereby, the processing circuitry 73 generates a mask image mk22 in which the surface shapes of the supporting frame 52 and the couch top 53 are rendered. Next, the processing circuitry 73 generates a synthesized image mk23 by synthesizing two mask images mk21 and mk22 to overlap each other, erasing the surface shape of the supporting frame 52, and rendering a curve Le connecting an end of the surface shape of the couch top 53 and an end of a curve of the subject P. Thereafter, the processing circuitry 73 generates the mask image mk2 by representing the interior of a closed curve included in the synthesized image mk23 as "1" indicating the region of the subject P, and representing the exterior of the closed curve as "0" indicating the artifact region. It is assumed that, at step ST52, the mask image mk2 has been generated.

After step ST52, at step ST53, as shown in FIG. 4, the processing circuitry 73 calculates a difference between the first binary image bin1 and the mask image mk2, and extracts an artifact region. That is, the processing circuitry 73 generates, based on the mask image mk2, a second binary image bin2 obtained by extracting, from a region relating to the subject P included in the first binary image bin1, an artifact region different from the region of the subject P, as shown in FIG. 8. In the first binary image bin1 in FIG. 8, the region relating to the subject P is represented as a white region "1", and the region different from the region relating to the subject P is represented as a black region "0". Also, in the mask image mk2, a region of the subject P is represented as a white region "1", and an artifact region is represented as a black region "0". Thereby, a differential computation is executed as one of the four computations <1> to <4> listed below.

<1> A computation of subtracting, from the black region "0" in the first binary image bin1, the black region "0" in the mask image mk2 (black-black=black(0) in the drawing).

<2> A computation of subtracting, from the white region "1" in the first binary image bin1, the black region "0" in the mask image mk2 (white-black=white(1) in the drawing).

<3> A computation of subtracting, from the white region "1" in the first binary image bin1, the white region "1" in the mask image mk2 (white-white=black(0) in the drawing).

<4> A computation of subtracting, from the black region "0" in the first binary image bin1, the white region "1" in the mask image mk2 (black-white=black(0)).

In the case of <4>, in place of a simple subtraction result "−1" (=0−1), a subtraction result "0" corresponding to the binary image is used for conformity with the binary values "0" and "1" of the second binary image bin2. The second binary image bin2 does not include a region of the subject P, and includes an artifact region representing artifacts atf and the couch top 53. The second binary image bin2 represents the artifact region in the region relating to the subject P in the first binary image bin1 as "1", and represents the region of the subject P as "0". Also, the second binary image bin2 represents the region relating to the subject P in the first binary image bin1 as "0". Since the second binary image bin2 is a binary image, in the second binary image bin2, a part of a region different from the region relating to the subject P in the first binary image bin1 becomes "−1", but is represented as "0". In FIG. 8, the dashed lines x1 and x2 correspond to the x-coordinate values of the mask image mk2, the first binary image bin1, and the second binary image bin2.

After step ST53, at step ST54, the processing circuitry 73 updates the X-ray CT image ct1 to remove, from the X-ray CT image ct1, a region corresponding to the artifact region "1" of the second binary image bin2, based on the second binary image bin2, as shown in FIGS. 4 and 9. The updated X-ray CT image ct2 includes a region of the subject P, and does not include a region of the artifacts atf and the couch top 53. Also, the processing circuitry 73 stores the updated X-ray CT image ct2 in the memory 75. With the foregoing, step ST50 including steps ST51 to ST54 ends.

Referring back to FIG. 3, at step ST60, the processing circuitry 73 synchronously controls the PET gantry 10 and the couch 50 in accordance with the acquisition area to which minor adjustments have been made at step ST20, and executes step-and-shoot PET imaging with the PET gantry 10. Through the PET imaging, coincidence-event data is acquired.

After step ST60, the processing circuitry 73 generates, at step ST70, an attenuation map based on the X-ray CT image updated at step ST50.

After step ST70, the processing circuitry 73 reconstructs, at step ST80, a PET image based on the attenuation map and the coincidence-event data. Thereafter, the processing circuitry 73 causes the display 74 to display the X-ray CT image and the PET image. Thereby, the PET/CT examination ends.

According to the first embodiment described above, an X-ray CT image relating to a subject is obtained, a camera image capturing the position and the shape of the subject corresponding to the X-ray CT image is obtained, and an attenuation map is generated based on the camera image and the X-ray CT image. Also, detection data based on gamma rays radiating from a radiation source administered into a subject is obtained, and an image is reconstructed based on the attenuation map and the detection data. By thus generating the attenuation map based on the X-ray CT image and the camera image capturing the position and the shape of the subject corresponding to the X-ray CT image, it is possible to reduce adverse effects, resulting from unintended structures included in the X-ray CT image, on the image.

It is to be added that, in three-dimensional X-ray CT image data (volume data), for example, artifacts (unintended structures) resulting from sinogram estimation in extended reconstruction may occur in an outer peripheral part of the subject, and be observed in all the directions outside the subject. This type of artifact is observed for every two-dimensional X-ray CT image obtained by slicing the volume data. If, for example, a two-dimensional X-ray CT image includes a portion at which an artifact occurs, the artifact is observed so as to extend from an outer peripheral part of the subject in the X-ray CT image. If, for example, a two-dimensional X-ray CT image is distanced from the portion at which the artifact occurs, the artifact is observed at a position slightly distanced from the subject in the X-ray CT image. In either case, artifacts in the X-ray CT image need to be reduced. According to the first embodiment, it is possible to reduce, from an X-ray CT image, both artifacts extending from an outer peripheral part of a subject and artifacts slightly distanced from the subject, based on a camera image. Accordingly, it is possible to improve the image quality and the quantitative values of the nuclear medicine diagnostic apparatus by reconstructing a nuclear medicine image based on an image with reduced artifacts.

Also, according to the first embodiment, an X-ray CT image is updated to remove, from the X-ray CT image, an artifact region different from a region of a subject based on a camera image, and an attenuation map is generated based on the updated X-ray CT image. By thus generating the attenuation map from the X-ray CT image from which the artifact region has been removed, it is possible to reduce adverse effects on a nuclear medicine image resulting from artifacts in the X-ray CT image, similarly to the above-described effect.

Moreover, according to the first embodiment, a first binary image is generated by binarizing an X-ray CT image according to whether or not each pixel falls in a region relating to the subject, and a mask image is generated by binarizing a camera image according to whether or not each pixel falls in a region of the subject. Moreover, a second binary image, in which an artifact region different from the region of the subject is extracted from the region relating to the subject included in the first binary image, is generated based on the mask image. Furthermore, an X-ray CT image is updated based on the second binary image to remove, from the X-ray CT image, a region corresponding to an artifact region of the second binary image. By thus performing processing using binary images, it is possible, in addition to the above-described effects, to remove, from the X-ray CT image, a region corresponding to the artifact region of the second binary image relatively easily.

Furthermore, according to the first embodiment, the first binary image may be a first attenuation map generated from the X-ray CT image. In this case, too, advantageous effects similar to the above-described effects are achieved.

Moreover, according to the first embodiment, the camera image further captures a couch on which a subject is placed. Moreover, a boundary between the subject and the couch is detected, based on the couch in the camera image and preset information relating to the shape of the couch, and a mask image is generated by regarding a side opposite to the subject relative to the boundary as a part of a region different from the subject. With the mask image being generated using the boundary between the subject and the couch, which are not shown in the camera image, it is possible, in addition to the above-described effects, to improve the accuracy of the mask image for removing the artifact region.

Furthermore, according to the first embodiment, a camera image is an image obtained by the processing circuitry 73 from at least one optical camera, 3D camera, infrared camera, ultrasonic sensor, or terahertz camera. With the camera image being obtainable from various cameras, etc., it is possible, in addition to the above-described effects, to achieve easy implementation.

Moreover, according to the first embodiment, since an image reconstructed based on an attenuation map and detection data is a PET image, it is possible to reduce an adverse effect on the PET image resulting from artifacts in an X-ray CT image, similarly to the above-described effect.

Furthermore, according to the first embodiment, since the nuclear medicine diagnostic apparatus is a PET/CT apparatus in which a PET apparatus and an X-ray CT apparatus are made integral, it is possible to reduce an adverse effect on the PET image resulting from artifacts in the X-ray CT image, similarly to the above-described effect.

In the first embodiment, the mask image mk2 generated in the case where the image imaged by the camera 60 contains distance information is used to extract an artifact region; however, the configuration is not limited thereto. As shown in FIG. 10, for example, the mask image mk1 generated in the case where the image imaged by the camera 60 does not contain distance information may be used to extract an artifact region. In the mask image mk1 in FIG. 10, the region of the subject P is represented as a white region "1", and the artifact region is represented as a black region "0". In this case, at step ST53, the processing circuitry 73 generates, based on the mask image mk1, a second binary image bin3 in which an artifact region different from the region of the subject P is extracted from the region relating to the subject P included in the first binary image bin1. A differential computation is executed by subtracting, from the black region "0" or the white region "1" in the first binary image bin1, the black region "0" or the white region "1" in the mask image mk1, similarly to the foregoing. Also, in the case of a computation of subtracting, from the black region "0" in the first binary image bin1, the white region "1" in the mask image mk1 (black-white=black(0) in the drawing), a subtraction result "0" corresponding to the binary image is used in place of a simple subtraction result "−1" (=0−1), similarly to the foregoing. The second binary image bin3 does not include the region of the subject P and the couch top 53, and includes an artifact region representing artifacts atf. The second binary image bin3 represents an artifact region in the region "1" relating to the subject P in the first binary image bin1 as "1", and represents a region of the subject P and the couch top 53 as "0". In FIG. 10, the dashed lines x1 and x2 correspond to the x-coordinate values of the mask image mk1, the first binary image bin1, and the second binary image bin3. Since the mask image mk1 is given only in one dimension, namely, the x-axis direction, the region of the couch top 53 positioned in a region at an x-coordinate overlapping the subject P is not extracted in the second binary image bin3, unlike the example of FIG. 8. However, compared to the artifacts atf in the X-ray CT image, the couch top 53 in the X-ray CT image has a small adverse effect on the nuclear medicine image. Accordingly, even with a mask image generated in the case where the image imaged by the camera 60 does not contain distance information, it is possible to obtain a similar advantageous effect that is slightly inferior to that of the first embodiment.

Second Embodiment

In the second embodiment, which is a modification of the first embodiment, an update is made not to an X-ray CT image but to an attenuation map generated from the X-ray CT image. Also, in the second embodiment, the attenuation map is updated not prior to the PET acquisition but as pre-processing of the PET reconstruction.

In accordance therewith, the processing circuitry 73 generates, with the attenuation map generating function 735, a first attenuation map from the X-ray CT image, and removes, from the first attenuation map, an artifact region different from a region of the subject P based on a camera image, thereby generating (updating) the attenuation map.

The attenuation map generating function 735 generates the first attenuation map by, for example, binarizing the X-ray CT image according to whether or not each pixel configuring the X-ray CT image falls in a region relating to the subject P. With the attenuation map generating function 735, a mask image is generated by binarizing the camera image according to whether or not each pixel configuring the mask image falls in a region of the subject P. With the attenuation map generating function 735, an attenuation map is generated by removing, from the region relating to the subject P included in the first attenuation map, an artifact region different from the region of the subject P, based on the mask image. In the case of removing the artifact region from the first attenuation map, the attenuation map generating function 735 sets, for example, the voxel value of the artifact region of the first attenuation map to 0.

The other configuration is similar to that of the first embodiment.

Next, an operation of the nuclear medicine diagnostic apparatus 1 with the above-described configuration will be described with reference to the flowcharts in FIGS. 11 and 13 and the schematic diagrams of FIGS. 12, 14, and 15.

As shown in FIG. 11, steps ST10 to ST30 are executed in a manner similar to the foregoing. Thereby, an image imaged by the camera 60 is stored in the memory 75, and an X-ray CT image by X-ray CT imaging is obtained by the processing circuitry 73.

After step ST30, step ST60 is executed, unlike the foregoing. At step ST60, the processing circuitry 73 synchronously controls the PET gantry 10 and the couch 50, and executes step-and-shoot PET imaging with the PET gantry 10. Through the PET imaging, coincidence-event data is acquired.

After step ST60, at step ST40a, the processing circuitry 73 obtains a camera image capturing the position and the shape of the subject P corresponding to the X-ray CT image. The processing circuitry 73 obtains a camera image by, for example, cutting a portion of an imaged image in the memory 75 at a position corresponding to that in the X-ray CT image.

After step ST40a, at step ST70a, the processing circuitry 73 generates a first attenuation map att1 by binarizing an X-ray CT image ct1 according to whether or not each pixel falls in a region relating to the subject P, as shown in FIGS. 11 and 12. The first attenuation map att1 represents the region relating to the subject P in the X-ray CT image ct1 as "1", and represents a region different from the region relating to the subject P as "0". The first attenuation map att1 includes, as the region relating to the subject P, a region representing the subject P, artifacts atf, and the couch top 53. It is to be added that, in the first attenuation map att1, a substantially oval region of the subject P exists at an approximate center, a region of artifacts atf exists on right and left sides of the subject P, and a region of the couch top 53 exists below the subject P. The supporting frame 52 that supports the couch top 53 is not slid into the PET/CT gantry 40, and is therefore not shown in the X-ray CT image ct1 and the first attenuation map att1.

After step ST70a, at step ST71a, the processing circuitry 73 generates an attenuation map by removing, from the first attenuation map att1, an artifact region different from the region of the subject P, based on the camera image. Step ST71a is executed by steps ST71a1 to ST71a2 as shown in FIGS. 13 to 15.

At step ST71a1, as shown in FIGS. 13 and 14, the processing circuitry 73 generates a mask image mk1a or mk2a by binarizing a camera image g2 obtained from an imaged image g1 according to whether or not each pixel falls in a region of the subject P. The mask images mk1a and mk2a represent the region of the subject P in the camera image g2 as "0", and represents an artifact region different from the region of the subject P as "1". The mask image mk1a is an example of the case where the imaged image g1 and the camera image g2 are two-dimensional images.

On the other hand, the mask image mk2a is a binarized image generated based on the camera image g2 in the case where the imaged image g1 and the camera image g2 contain distance information. The camera image g2 further captures the couch 50 on which the subject P is placed. In this case, the processing circuitry 73 detects, based on, for example, the couch 50 in the camera image g2 and preset information relating to the shape of the couch 50, a boundary between the subject P and the couch 50, and generates a mask image mk2a by regarding a side opposite to the subject P relative to the boundary as a part of a region different from the subject P. As shown in FIG. 7, for example, the mask image mk2a is generated by generating images mk21 and mk22 and a synthesis image mk23, with the interior of a closed curve included in the synthesized image mk23 represented as "0" indicating the region of the subject P, and the exterior of the closed curve represented as "1" indicating the artifact region. It is assumed that, at step ST71a1, the mask image mk2a has been generated.

After step ST71a1, at step ST71a2, the processing circuitry 73 calculates a difference between the first attenuation map att1 and the mask image mk2a, and removes the artifact region, as shown in FIG. 15. In FIG. 15, the dashed lines x1 and x2 correspond to the x-coordinate values of the mask image mk2a, the first attenuation map att1, and the attenuation map att2. That is, the processing circuitry 73 generates the attenuation map att2 by removing, from the region relating to the subject P included in the first attenuation map att1, the artifact region different from the region of the subject P, based on the mask image mk2a. A differential computation is executed by subtracting, from the black region "0" or the white region "1" in the first attenuation map att1, the black region "0" or the white region "1" in the mask image mk2a, similarly to the foregoing. Also, in the case of a computation of subtracting, from the black region "0" in the first attenuation map att1, the white region "1" in the mask image mk2a (black-white=black(0) in the drawing), a subtraction result "0" corresponding to the binary image is used in place of a simple subtraction result "−1" (=0−1), similarly to the foregoing. The attenuation map att2 includes the region of the subject P, and does not include an artifact region representing artifacts atf and the couch top 53. The attenuation map att2 represents the region of the subject P in the attenuation map att1 as "1", and represents the artifact region as "0". The processing circuitry 73 updates the first attenuation map att1 to an attenuation map att2, and stores the updated attenuation map att2 in the memory 75. With the foregoing, step ST71a including steps ST71a1 to ST71a2 ends.

Referring back to FIG. 11, after step ST71a, the processing circuitry 73 reconstructs, at step ST80, a PET image based on the updated attenuation map and the coincidence-event data. Thereafter, the processing circuitry 73 causes the display 74 to display the X-ray CT image and the PET image. Thereby, the PET/CT examination ends.

As described above, according to the second embodiment, a first attenuation map is generated from an X-ray CT image, and an artifact region different from the region of the subject is removed from the first attenuation map based on a camera image, and thereby an attenuation map is generated. Accordingly, it is possible, in addition to the effects of the first embodiment, to reduce the artifact region in the attenuation map as pre-processing of the PET reconstruction, without updating the X-ray CT image prior to PET imaging. Also, based on the attenuation map with reduced artifacts, it is possible to improve the image quality and the quantitative values of the nuclear medicine diagnostic apparatus by reconstructing a nuclear medicine image.

Moreover, according to the second embodiment, a first attenuation map is generated by binarizing an X-ray CT image according to whether or not each pixel falls in a region relating to the subject, and a mask image is generated by binarizing a camera image according to whether or not each pixel falls in a region of the subject. Also, an attenuation map is generated by removing, from the region relating to the subject P included in the first attenuation map, an artifact region different from the region of the subject, based on the mask image. By thus performing processing using a binarized mask image, it is possible to remove the artifact region from the attenuation map relatively easily.

In the second embodiment, the mask image mk2a generated in the case where the image imaged by the camera 60 contains distance information is used to extract an artifact region; however, the configuration is not limited thereto. As shown in FIG. 16, for example, the mask image mk1a generated in the case where the image imaged by the camera 60 does not contain distance information may be used to extract an artifact region. In the mask image mk1a in FIG. 16, the region of the subject P is represented as a black region "0", and the artifact region is represented as a white region "1". In this case, the processing circuitry 73 generates an attenuation map att3 by partially removing, from the region relating to the subject P included in the first attenuation image att1, an artifact region different from the region of the subject P, based on the mask image mk1a. A differential computation is executed by subtracting, from the black region "0" or the white region "1" in the first attenuation map att1, the black region "0" or the white region "1" in the mask image mk1a, similarly to the foregoing. Also, in the case of a computation of subtracting, from the black region "0" in the first attenuation map att1, the white region "1" in the mask image mk1a (black-white=black(0) in the drawing), a subtraction result "0" corresponding to the binary image is used in place of a simple subtraction result "−1" (=0−1), similarly to the foregoing. The attenuation map att3 does not include a region of artifacts atf in the artifact region, and includes a region of the couch top 53, in addition to the region of the subject P. The attenuation map att3 represents an artifact region in the region "1" relating to the subject P in the first attenuation map att1 as "0", and represents a region of the subject P and the couch top 53 as "1". In FIG. 16, the dashed lines x1 and x2 correspond to the x-coordinate values of the mask image mk1, the first attenuation map att1, and the attenuation map att3. Since the mask image mk1a is given only in one dimension, namely, the x-axis direction, the region of the couch top 53 positioned in a region at an x-coordinate overlapping the subject P is not removed from the attenuation map att3, unlike the example of FIG. 15. However, compared to the artifacts atf in the X-ray CT image, the couch top 53 in the X-ray CT image has a small adverse effect on the nuclear medicine image. Accordingly, even with a mask image generated in the case where the image imaged by the camera 60 does not contain distance information, it is possible to obtain a similar advantageous effect that is slightly inferior to that of the second embodiment.

In the second embodiment, after coincidence-event data is acquired by PET imaging, an artifact region is removed from an attenuation map; however, the configuration is not limited thereto. After the acquisition of the coincidence-event data by PET imaging, a process of obtaining a camera image corresponding to an X-ray CT image (step ST40a) and a process of updating an X-ray CT image based on the camera image (step ST50a) may be executed, as shown, for example, in FIG. 17. Steps ST40a and St50a are similar to steps ST40 and ST50 in the first embodiment. In such a modification, it is also possible, in addition to the effects of the first embodiment, to reduce an artifact region in an attenuation map as pre-processing of the PET reconstruction, without updating an X-ray CT image prior to PET imaging.

In the first and second embodiments, the subject P is imaged with only the camera 60 arranged on the ceiling above the couch 50; however, the configuration is not limited thereto. As shown in FIG. 18, the subject P may be imaged from above and from the side using two cameras, such as a camera 60 arranged on the ceiling and a camera 60 arranged on a wall w1 lateral to the couch 50. It is to be noted that the added camera 60 is, for example, installed on a wall w1 so as to be positioned lateral to the couch 50 and the rotation axis Z, and to allow a direction orthogonally intersecting the rotation axis Z to be a direction of imaging. On a lateral side of the supporting frame 52 of the couch 50, a linear part Lb indicating a height of a bottom part 53b of the couch top 53 may be formed, as shown in FIGS. 18 and 19, and an upper lateral surface and a lower lateral surface, between which a boundary is formed by the linear part Lb, may be differently colored. However, the configuration is not limited thereto, and the height of the bottom part 53b of the couch top 53 may be calculated, from an imaged image in which a lateral side of the supporting frame 52 is imaged, based on a preset height difference between a top part of the supporting frame 52 and a bottom part 53b of the couch top 53. The position at which each camera 60 is installed is recorded in the console 70 in advance. In this case, as each of the two cameras, a camera not having distance information, such as an optical camera, an infrared camera, a terahertz camera, etc., for example, can be suitably employed. However, the configuration is not limited thereto, and two cameras having distance information may be provided, for improvement in the precision of a mask image. In the case of an optical camera, an infrared camera, or a terahertz camera, the image to be imaged will be a 2D image including a region representing a position and a shape of the subject P and an external region different from said region. Also, a camera image cut from the imaged image will also be a two-dimensional image.

Accordingly, at ST52 of the first embodiment, the processing circuitry 73 generates a mask image mk1 by binarizing a camera image g2 obtained from an imaged image g1 imaged by the camera 60 arranged on the ceiling, as shown in FIG. 6, according to whether or not each pixel falls in a region of the subject P. In addition thereto, at ST52, the processing circuitry 73 generates a mask image mk3 by binarizing a camera image g4 obtained from an imaged image g3 imaged by the camera 60 arranged on the wall w1, as shown in FIG. 20, according to whether or not each pixel falls in the region of the subject P. It is to be noted that, of an upper region and a lower region that are not the region of the subject P in the mask image mk3, the lower region is a region below the linear part Lb. The mask image mk3 represents a region of the subject P in the camera image g4 as "1", and represents an artifact region different from the region of the subject P as "0".

Also, at step ST53, the processing circuitry 73 generates, based on a mask image mk1, a second binary image bin3 in which an artifact region "1" different from the region of the subject P is extracted from the region "1" relating to the subject P included in the first binary image bin1, as shown in FIG. 10. In addition thereto, at step ST53, the processing circuitry 73 generates, based on a mask image mk3, a second binary image bin4 in which an artifact region "1" different from the region of the subject P is extracted from the region "1" relating to the subject P included in the first binary image bin1, as shown in FIG. 21. In the second binary image bin4, a region of the subject P, the artifacts aft, and the couch top 53 above the bottom part of the couch top 53 in the region "1" relating to the subject P in the first binary image bin1 is represented as a black region "0", and a region below the bottom part of the couch top 53 is represented as a white region "1". The white region "1" below the bottom part of the couch top 53 is an artifact region "1" in the second binary image bin4. The bottom part of the couch top 53 may also be referred to as a "bottom part of the subject P".

Thereafter, at step ST54, the X-ray CT image ct1 is updated to remove, from the X-ray CT image ct1, a region corresponding to the artifact region "1" of the second binary images bin3 and bin4, based on two second binary images bin3 and bin4, as shown in FIG. 22. The updated X-ray CT image ct3 includes a region of the subject P, and does not include a region of the artifacts atf and the couch top 53 below the bottom part 53b of the couch top 53. Also, the processing circuitry 73 stores the updated X-ray CT image ct3 in the memory 75. The subsequent processing is executed in a manner similar to the first embodiment. Accordingly, the artifact region can be removed over a slightly broader range than in the example of FIG. 10, by an area corresponding to the artifact region "1" in the second binary image bin4, as shown in FIG. 22.

On the other hand, in the case of application to the second embodiment, at step ST71a1, the processing circuitry 73 generates a mask image mk1a by binarizing a camera image g2 obtained from an imaged image g1 imaged by the camera 60 arranged on the ceiling, as shown in FIG. 14, according to whether or not each pixel falls in a region of the subject P. In addition thereto, at ST71a1, the processing circuitry 73 generates a mask image mk3a by binarizing a camera image g4 obtained from an imaged image g3 imaged by the camera 60 arranged on the wall w1, as shown in FIG. 20, according to whether or not each pixel falls in the region of the subject P. Of an upper region and a lower region that are not the region of the subject P in the mask image mk3a, the lower region is a region below the linear part Lb. The mask image mk3a represents a region of the camera image g4 of the subject P as "0", and represents an artifact region different from the region of the subject P as "1".

At step ST71a2, the processing circuitry 73 generates an attenuation map att3 by removing, from the region relating to the subject P in the first attenuation map att1, an artifact region different from the region of the subject P, based on the mask image mk1a, as shown in FIG. 16. In addition thereto, at step ST71a2, the processing circuitry 73 generates an attenuation map att4 by removing, from the region relating to the subject P included in the attenuation map att3, an artifact region different from the region of the subject P, based on the mask image mk3a, as shown in FIG. 23. The generated attenuation map att4 includes a region of the subject P, and does not include a region of the artifacts atf and the bottom part 53b below the bottom part 53b of the couch top 53. In the attenuation map att4, a region of the subject P, the artifacts aft, and the couch top 53 above the bottom part of the couch top 53 of the region "1" relating to the subject P in the attenuation map att3 is represented as a white region "1", and a region below the bottom part of the couch top 53 is represented as a black region "0". Accordingly, the artifact region can be removed over a slightly broader range than in the example of FIG. 16, since the region below the bottom part 53b of the couch top 53 is not included, as shown in FIG. 23.

In the first and second embodiments and the modifications thereof, a case has been discussed where the nuclear medicine diagnostic apparatus is a PET/CT apparatus, and a nuclear medicine image is a PET image; however, the configuration is not limited thereto, as described above. If, for example, the nuclear medicine diagnostic apparatus is a SPECT/CT apparatus in which a SPECT apparatus and an X-ray CT apparatus are made integral, and the nuclear medicine image is a SPECT image, advantageous effects similar to those of the first and second embodiments can be obtained.

Also, in the first and second embodiments and the modifications thereof, a case has been described as an example where the nuclear medicine diagnostic apparatus is a PET/CT apparatus; however, the configuration is not limited thereto. For example, the nuclear medicine diagnostic apparatus may be realized by one of a PET apparatus, a SPECT apparatus, and a SPECT/CT apparatus in which a SPECT apparatus and an X-ray CT apparatus are made integral. FIG. 24 shows a configuration in the case where, for example, the nuclear medicine diagnostic apparatus 1 is a PET apparatus. In the nuclear medicine diagnostic apparatus 1 in FIG. 24, a configuration relating to the CT apparatus such as the CT gantry 30, the CT data memory 72, etc. are omitted, and a CT image obtaining function 733a is added to the processing circuitry 73, relative to the configuration of the PET/CT apparatus shown in FIG. 1. The CT image obtaining function 733a obtains an X-ray CT image relating to the subject P imaged by means of X-ray CT by a CT apparatus (not illustrated) separate from the nuclear medicine diagnostic apparatus 1, and stores the X-ray CT image in the memory 75. Specifically, with the CT image obtaining function 733a, the processing circuitry 73 obtains an X-ray CT image relating to the subject P via an unillustrated network from an exterior CT apparatus or a server apparatus. The CT image obtaining function 733a and the processing circuitry 73 are other examples of the CT image obtaining unit. The other configuration is similar to those of the first and second embodiments. In this manner, even if the nuclear medicine diagnostic apparatus 1 is a PET apparatus configured to obtain an X-ray CT image from the outside, it is possible to obtain similar advantageous effects as can be obtained by the first and second embodiments. The same applies to the case where the nuclear medicine diagnostic apparatus 1 is a SPECT apparatus, and an image to be reconstructed (nuclear medicine image) is a SPECT image.

According to at least one of the above-described embodiments, it is possible to reduce adverse effects, resulting from intended structures included in an X-ray CT image, on the image.

The term "processor" used herein means, for example, circuitry such as a central processing unit (CPU), a graphics processing unit (GPU), or circuitry such as an application-specific integrated circuit (ASIC), a programmable logic device (e.g., or a simple programmable logic device (SPLD), a complex programmable logic device (CPLD), etc.), or a field-programmable gate array (FPGA), etc. If the processor is, for example, a CPU, the processor reads and executes programs stored in storage circuitry to realize the functions. If the processor is, for example, an ASIC, the functions are directly incorporated into the circuitry of the processor as logic circuitry, instead of the programs being stored in the storage circuitry. Each processor in the present embodiment is not limited to a single circuitry-type processor, and multiple independent circuits may be combined and integrated as a single processor to realize the intended functions. Furthermore, multiple components or features as given in FIG. 1 or 24 may be integrated as a single processor to realize the respective functions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A nuclear medicine diagnostic apparatus, comprising:
processing circuitry configured to:
obtain an X-ray CT image relating to a subject;
obtain a camera image capturing a position and a shape of the subject corresponding to the X-ray CT image;
generate an attenuation map based on the camera image and the X-ray CT image;
obtain detection data based on gamma rays radiating from a radiation source administered into the subject; and
reconstruct an image based on the attenuation map and the detection data,
wherein the processing circuitry is further configured to:
update the X-ray CT image to remove, from the X-ray CT image, an artifact region different from a region of the subject, based on the camera image; and
generate the attenuation map based on the updated X-ray CT image.

2. The nuclear medicine diagnostic apparatus according to claim 1, wherein the processing circuitry is further configured to:
generate a first binary image by binarizing the X-ray CT image according to whether or not each pixel of the X-ray CT image falls in the region of the subject;
generate a mask image by binarizing the camera image according to whether or not each pixel of the camera image falls in the region of the subject;
generate a second binary image in which the artifact region different from the region of the subject is extracted, based on the mask image, from the region relating to of the subject included in the first binary image; and
update the X-ray CT image based on the second binary image to remove, from the X-ray CT image, a region corresponding to the artifact region of the second binary image.

3. The nuclear medicine diagnostic apparatus according to claim 2, wherein
the camera image further captures a couch on which the subject is placed, and
the processing circuitry is further configured to detect a boundary between the subject and the couch, based on the couch in the camera image and preset information relating to a shape of the couch, and generate the mask image by regarding a side opposite to the subject relative to the boundary as a part of another region different from the region of the subject.

4. The nuclear medicine diagnostic apparatus according to claim 2, wherein the first binary image is a first attenuation map generated from the X-ray CT image.

5. The nuclear medicine diagnostic apparatus according to claim 1, wherein the camera image is an image obtained by the processing circuitry from at least one optical camera, a 3D camera, an infrared camera, an ultrasonic sensor, or a terahertz camera.

6. The nuclear medicine diagnostic apparatus according to claim 1, wherein the image to be reconstructed is either a PET image or a SPECT image.

7. The nuclear medicine diagnostic apparatus according to claim 1, wherein the nuclear medicine diagnostic apparatus is at least one of a PET apparatus, a SPECT apparatus, a PET/CT apparatus in which a PET apparatus and an X-ray CT apparatus are made integral, or a SPECT/CT apparatus in which a SPECT apparatus and an X-ray CT apparatus are made integral.

8. A nuclear medicine diagnostic apparatus, comprising:
processing circuitry configured to
obtain an X-ray CT image relating to a subject:
obtain a camera image capturing a position and a shape of the subject corresponding to the X-ray CT image;
generate an attenuation map based on the camera image and the X-ray CT image;
obtain detection data based on gamma rays radiating from a radiation source administered into the subject; and
reconstruct an image based on the attenuation map and the detection data,
wherein the processing circuitry is further configured to:
generate a first attenuation map by binarizing the X-ray CT image according to whether or not each pixel of the X-ray CT image falls in a region of the subject;
generate a mask image by binarizing the camera image according to whether or not each pixel of the camera image falls in the region of the subject; and
generate the attenuation map by removing, from the region of the subject included in the first attenuation map, an artifact region different from the region of the subject, based on the mask image.

9. A nuclear medicine diagnostic method, comprising:
obtaining an X-ray CT image relating to a subject;
obtaining a camera image capturing a position and a shape of the subject corresponding to the X-ray CT image;
generating an attenuation map based on the camera image and the X-ray CT image;
obtaining detection data based on gamma rays radiating from a radiation source administered into the subject; and
reconstructing an image based on the attenuation map and the detection data,
wherein the method further comprises:
updating the X-ray CT image to remove, from the X-ray CT image, an artifact region different from a region of the subject, based on the camera image; and
generating the attenuation map based on the updated X-ray CT image.

10. A non-transitory computer readable storage medium including computer executable instructions, wherein the instructions, when executed by a processor, cause the processor to perform a method comprising:
obtaining an X-ray CT image relating to a subject;
obtaining a camera image capturing a position and a shape of the subject corresponding to the X-ray CT image;
generating an attenuation map based on the camera image and the X-ray CT image;

obtaining detection data based on gamma rays radiating from a radiation source administered into the subject; and reconstructing an image based on the attenuation map and the detection data, wherein the method further comprises:

updating the X-ray CT image to remove, from the X-ray CT image, an artifact region different from a region of the subject, based on the camera image; and generating the attenuation map based on the updated X-ray CT image.

* * * * *